(12) United States Patent
Ruiz

(10) Patent No.: US 6,547,393 B2
(45) Date of Patent: *Apr. 15, 2003

(54) INTERACTIVE CORRECTIVE EYE SURGERY SYSTEM WITH TOPOGRAPHY AND LASER SYSTEM INTERFACE

(76) Inventor: Luis Antonio Ruiz, Contro Ofulmólogico Colombiano, Carrera 20 No. 85-11, Pisos 5o.-6o., Santa de Bogorá D.C. (CO)

(*) Notice: Subject to any disclaimer, the term of this patent is extended or adjusted under 35 U.S.C. 154(b) by 0 days.

This patent is subject to a terminal disclaimer.

(21) Appl. No.: 09/955,300

(22) Filed: Sep. 19, 2001

(65) Prior Publication Data

US 2002/0075451 A1 Jun. 20, 2002

Related U.S. Application Data

(63) Continuation of application No. 09/525,424, filed on Mar. 14, 2000, now Pat. No. 6,299,309, which is a continuation of application No. 09/267,926, filed on Mar. 10, 1999, now Pat. No. 6,129,722.

(51) Int. Cl.[7] .................................................. A61B 3/10
(52) U.S. Cl. ........................................... 351/212; 606/5
(58) Field of Search ................................ 351/205, 211, 351/212, 221, 246, 208; 606/4, 5

(56) References Cited

U.S. PATENT DOCUMENTS

| | | | |
|---|---|---|---|
| 4,665,914 A | 5/1987 | Tanne | 128/305 |
| 4,669,466 A | 6/1987 | L'Esperance | 128/303.1 |
| 4,691,716 A | 9/1987 | Tanne | 128/774 |

(List continued on next page.)

FOREIGN PATENT DOCUMENTS

| | | |
|---|---|---|
| EP | 0910984 | 4/1999 |
| WO | WO 9933393 | 7/1990 |
| WO | WO 97/46183 | 12/1997 |
| WO | WO 98/24364 | 6/1998 |
| WO | WO 98/48746 | 11/1998 |
| WO | WO 9962397 | 12/1999 |

OTHER PUBLICATIONS

Sher, Neila, Surgery for Hyperopia & Presbyopia; Chapter 3 and 5.

Manns, Fabrice, "Development of an Algorithm for Corneal Reshaping with a Scanning Laser Beam", *Applied Optics*, 34, 4600–08 (Jul. 1995).

Ren, Quishi, et al. "Laser Refractive Surgery: A Review and Current Status", *Optical Engineering*, 34 64 59 (1995).

*Corneal Topography—The State of the Art,* James P. Gill et al. Chapters 3, 5, 7, 9 and 16.

Lin, J.T. "Critical Review of Refractive Surgical Lasers", *Optical Engineering*, 34, 668–75 (1995).

(List continued on next page.)

*Primary Examiner*—George Manuel
(74) *Attorney, Agent, or Firm*—Smith, Gambrell & Russell

(57) ABSTRACT

A system and method for correcting corneal irregularities through reshaping of an eye's cornea to provide a desired corrective corneal curvature. A preferred embodiment of the invention includes a topography device for mapping in detail the irregularities and surface deviations of a cornea, an interface system for receiving and manipulating topographical data and for providing directions to a laser system or the like to carry out a predetermined ablation profile on a substrate such as a corneal stroma and for providing a variety of actual and simulated pre and post operative visual depictions. The interface system, which can be a stand alone item, provides a tool for use by a surgeon or the like which allows a surgeon to input his expertise in the development of a clinical ablation profile that is well suited for the eye characteristics, review and also simulate a wide variety of potential surgical alternatives for a wide variety of corneal defects including irregular eye shapes and corneal surface irregularities.

23 Claims, 42 Drawing Sheets

U.S. PATENT DOCUMENTS

| | | |
|---|---|---|
| 4,721,379 A | 1/1988 | L'Esperance |
| 4,911,711 A | 3/1990 | Telfair et al. |
| 4,995,716 A | 2/1991 | Warnicki et al. |
| 5,106,183 A | 4/1992 | Yoder, Jr. |
| 5,159,361 A | 10/1992 | Cambier et al. |
| 5,318,046 A | 6/1994 | Rozakis |
| 5,521,657 A | 5/1996 | Klopotek .................... 351/212 |
| 5,533,997 A | 7/1996 | Ruiz |
| 5,571,107 A | 11/1996 | Shaibani et al. ............... 606/4 |
| RE35,421 E | 1/1997 | Ruiz et al. |
| 5,610,709 A | 3/1997 | Arrington et al. |
| 5,640,962 A | 6/1997 | Jean et al. .................. 128/664 |
| 5,695,509 A | 12/1997 | El Hage ..................... 606/166 |
| 5,740,815 A | 4/1998 | Alpins ....................... 128/897 |
| 5,741,245 A | 4/1998 | Cozean et al. ................. 606/5 |
| 5,843,070 A | 12/1998 | Cambier et al. |
| 5,873,832 A | 2/1999 | Maloney et al. ............ 600/473 |
| 5,891,131 A | 4/1999 | Rajan et al. ................... 606/5 |
| 5,891,132 A | 4/1999 | Hohla ........................... 606/5 |
| 5,904,678 A | 5/1999 | Pop |
| 5,920,373 A | 7/1999 | Bille .......................... 351/212 |
| 5,928,129 A | 7/1999 | Ruiz ............................ 600/5 |
| 5,953,100 A | 9/1999 | Sarver et al. |
| 5,975,084 A | 11/1999 | Alpins ....................... 128/897 |
| 5,997,529 A | 12/1999 | Tang et al. |
| 6,010,497 A | 1/2000 | Tang et al. |
| 6,022,107 A | 2/2000 | Kutschbach et al. ........ 351/200 |
| 6,116,737 A | 9/2000 | Kern |
| 6,129,722 A | 10/2000 | Ruiz |
| 6,132,424 A | 10/2000 | Tang |
| 6,210,169 B1 | 4/2001 | Yavitz |
| RE37,504 E | 1/2002 | Lin |
| 2001/0031959 A1 | 10/2001 | Rozakis et al. |
| 2001/0033362 A1 | 10/2001 | Sarver |
| 2001/0053906 A1 * | 12/2001 | Odrich et al. .................. 606/5 |
| 2001/0055095 A1 | 12/2001 | D-Souza et al. |
| 2002/0013579 A1 | 1/2002 | Silvestrini |
| 2002/0026181 A1 | 2/2002 | O'Donnell, Jr. |

OTHER PUBLICATIONS

Munnerlyn, Charles R., et al., "Development of an Algorithm for Corneal Reshaping With a Scanning Las Beam", *Applied Optics,* 34, 4600–08 (Jul. 1995).

Provisional application No. 60/076,786, filed Mar. 4, 1998.

Scerra, Chet, "Corneal Topography," Ophthalmology Times, Jun. 1, 2001.

Web printouts of AstraMax product on www.lase.com, with a date of 2000.

* cited by examiner

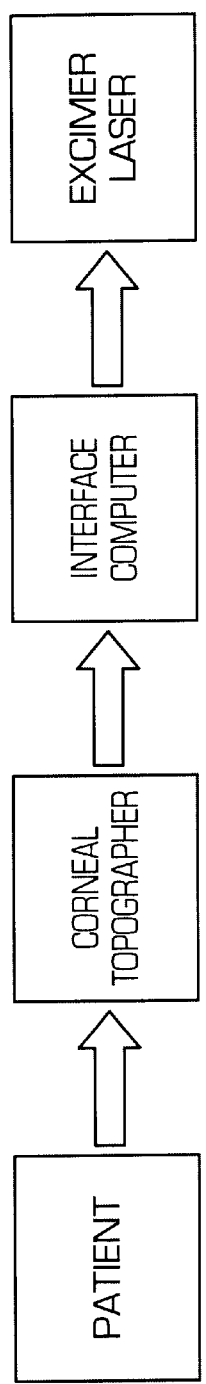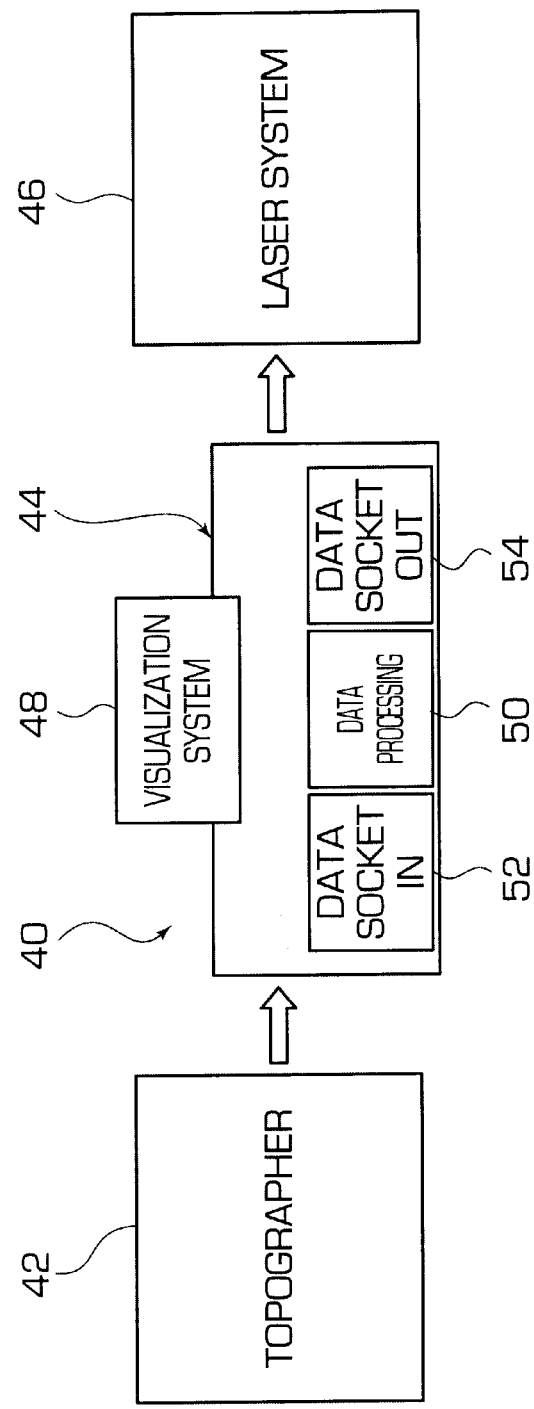

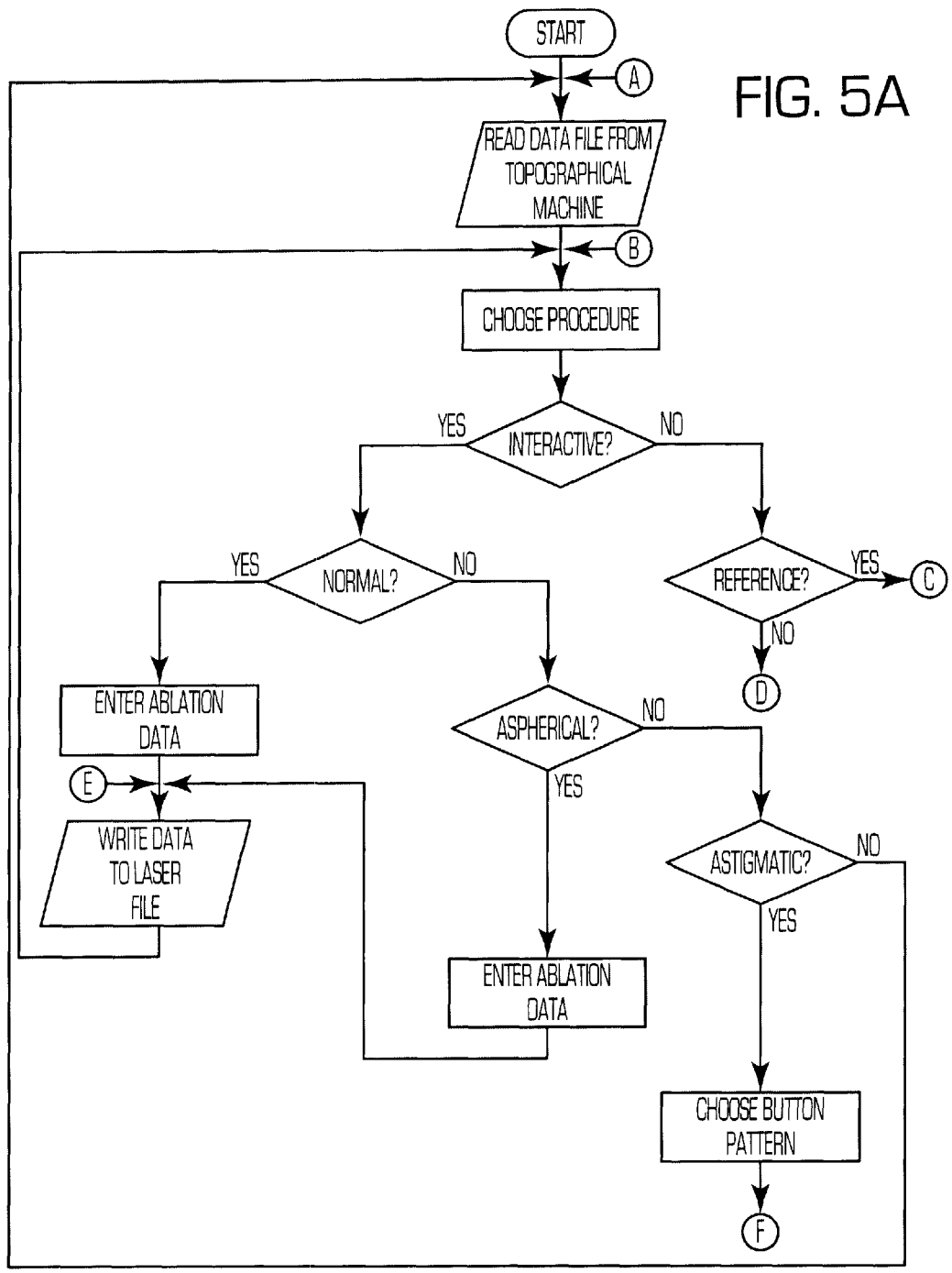

FIG. 27A  f=500   $ax^2-bx^4-cy^4+d\pm fx^2y$

FIG. 27B  f=500   $ax^2-bx^4-cy^4+d\pm fxy^2$

FIG. 27C  f=5   $ax^2-bx^4-cy^4+d\pm fxy$

FIG. 27D   $ax^2-bx^4-cy^4+d\pm gxy^{2-2}$

FIG. 27E   $ax^2-bx^4-cy^4+d+hy$

FIG. 27F   $ax^2-bx^4-cy^4+d+hy-fxy$

INTERACTIVE CORRECTIVE EYE SURGERY SYSTEM WITH TOPOGRAPHY AND LASER SYSTEM INTERFACE

CROSS REFERENCE TO RELATED APPLICATION(s)

This application is a continuation of prior application Ser. No. 09/525,424, filed Mar. 14, 2000, now U.S. Pat. No. 6,299,309 which is a continuation of 09/267,926, filed Mar. 10, 1999, which is now U.S. Pat. No. 6,129,722, each of which is incorporated in its entirety herein by reference.

FIELD OF THE INVENTION

The invention relates to a system and method for correcting corneal irregularities through reshaping of an eye's cornea to provide a desired corrective corneal curvature. A preferred embodiment of the invention includes a topography device for mapping in detail the irregularities and surface deviations of a cornea, an interface system for receiving and manipulating topographical data and for providing directions to a laser system or the like to carry out a predetermined ablation profile on a substrate such as a corneal stroma and for providing a variety of actual and simulated pre and post operative visual depictions. The interface system provides a tool for use by a surgeon or the like which allows a surgeon to review and simulate a wide variety of potential surgical alternatives for a wide variety of corneal defects including irregular eye shapes and corneal surface irregularities.

BACKGROUND OF THE INVENTION

For many, many years, humans have sought ways to correct visual problems. The ancient Chinese slept with small bags of mercury on their eyes, flattening their corneas and improving their shortsightedness. Unfortunately, the effects only worked for a few minutes after waking. Spectacles are thought to have been first introduced by the Arabs in the 11th Century and were introduced into Europe about 200 years later. This century has seen the development of contact lenses, initially the hard variety and later soft and disposable soft lenses.

Although these optical aids allow patients to see well while wearing them, they do not offer a permanent cure for the visual disorder or problem, and in some situations even glasses and contacts cannot provide complete correction due, for example, to a localized, highly irregular shaped corneal defect. Also, in many situations, they are inappropriate, for example, when swimming or wearing contacts in the laboratory. Another problem is that in some instances dangerous situations can arise when they become dislodged. This can occur while they are being used by firefighters and police officers.

Roughly two decades ago, surgical techniques were introduced in an effort to permanently correct shortsightedness and astigmatism. The radial keratotomy procedure used a diamond blade to make incisions into the cornea, the front surface or "window of the eye". Although this technique worked relatively well, there have been problems with long term stability of vision and weakening of the cornea as a result of the cuts often having to be made up to 95% of the corneal thickness.

More recently, these older techniques have been replaced with laser treatment techniques which have replaced the surgeon's blade with a computer controlled laser that gently re-sculptures the shape of the cornea without cutting or, for most applications, weakening the eye. These laser techniques are typically carried out with a photoablation process using an excimer laser.

Excimer lasers were chiefly developed for the manufacture of computer microchips, where they were used to etch the circuits. However, the laser's extreme accuracy and low thermal effect resulted in it being well suited as an eye laser. That is, many eye lasers are extremely accurate and remove only 0.25 microns (1/4000$^{th}$ millimeter) of tissue per pulse. During the re-sculpturing, the excimer laser gently "evaporates" or vaporizes tissue; there is no burning or cutting involved. In most cases, the laser treatment takes only 20 to 45 seconds, depending on how severe the refractive error is. A fast treatment time is important in that, for some procedures, an overextended treatment period can slow the post operative curing process to final vision level obtainment.

In the normal eye, light rays entering the eye are accurately focused on the retina and a clear image is formed. Most of the bending or focusing of the light rays occurs at the cornea, with the natural lens inside the eye being responsible for fine adjustments. If light is not focused on the retina, then the eye is said to have a refractive error. Common refractive errors include: myopia or shortsightedness, hyperopia or farsightedness, and astigmatism. The excimer laser has been used to re-sculpture the cornea in myopia, hyperopia and astigmatism corrections in an effort to make the curve of the cornea focus light rays normally on the retina.

Myopia, or shortsightedness, is a condition whereby light rays come to a focus in front of, rather than on, the retina at the back of the eye. This results in blurry vision, especially when looking at objects far away. Myopia results from the length of the eye being too long or the cornea being too steeply curved.

In hyperopia, or farsightedness, light rays are focused behind the retina. This results in blurry vision especially when looking at objects that are close. Hyperopia results from the length of the eye being too short or the cornea being too flat.

In astigmatism, the cornea, or window of the eye, has an irregular curvature being shaped more like a rugby ball, rather than a soccer ball. Light rays are focused at different points. A person often has some degree of astigmatism and myopia or hyperopia at the same time. Any surface contour irregularities can also result in the improper focusing of the eye due to the irregularities causing light rays to land away from the desired focal point on the retina.

In myopia laser correction procedures, the cornea is flattened to better focus light rays normally on the retina, whereas in hyperopia, the cornea is made more curved. With astigmatism, the surface of the cornea is re-sculptured to a regular curvature.

Presbyopia is a problem considered to be due to an aging process occurring in the natural lens of the eye, and thus does not fall under the same category as the refractive errors of myopia, astigmatism and hyperopia noted above, although combinations of presbyopia and one or more of the refractive errors are possible. U.S. Pat. No. 5,533,997 to Dr. Luis A. Ruiz describes a presbyopia corrective apparatus and method which involves the use of a laser system to remove tissue from the eye in presbyopic corrective patterns discovered to be effective by the inventor.

One of the prior art laser treatment methods is known as photorefractive keratectomy (PRK), in which the laser beam is applied directly to the surface of the cornea, after the thin surface layer of epithelium cells has been removed (e.g., through solvent with wiping, preliminary laser treatment, or minor abrasion). After the direct laser re-sculpturing of the cornea, a bare area of the cornea is left which takes a few days to heal (e.g., 2 to 6 days) and can be uncomfortable during this period. The healing process can sometimes lead to regression (some refractive error returns) or to scarring (which may blur the vision), especially in patients with large refractive errors. Although still used for low degrees of myopia and hyperopia, PRK is generally being replaced by the LASIK method for these same disorders, in which the laser treatment is applied under a protective corneal flap. Under the "Laser in situ Keratomileusis" (LASIK) treatment, a thin protective corneal flap is raised, rather like a trapdoor. The front surface of the exposed cornea is treated by the excimer laser. The net result being that the cornea is altered in a manner directed at allowing light rays to be focused normally on the retina. At the end of the procedure, the protective flap is simply replaced. The LASIK technique leaves the original surface of the cornea virtually intact, hence, there is no bare area to cause pain. In addition, the mild healing process results in minimal regression and avoids scarring problems.

The ablation profiles for the prior art PRK and LASIK laser treatments described above are based on mathematical equations and formulas that assume the eye as a perfect optical body or one that conforms to an optical model having very regular spherical shapes. The prior art ablation profiles thus fail to take into consideration the fact that each eye is unique and possesses many individual and general small and large irregularities. Because the prior art ablation profiles are based on fixed and regular ablation patterns, there can be created situations where excessive tissue is removed or insufficient tissue is removed. For example, in certain astigmatism situations there is a much larger defect on one side as compared to the opposite diametrical side. Thus, upon application of a normal, prior art laser ablation pattern for such a situation (an eliptical ablation profile), the ablation pattern would remove both the tissue causing the defect and tissue not associated with the defect, thus creating the possibility of a new defect in the eye following treatment.

Also, the corneal surface is not a very smooth body and has topographical irregularities which can be both large and small. Under the prior art laser systems these surface irregularities are not taken into consideration in the formulas and patterns designed to correct defects such as hyperopia, myopia and astigmatism. Accordingly, the final ablation profile formed in the eye will deviate to some extent from what was predetermined by the surgeon to be the final resultant profile of the eye, and this is particularly true with respect to eyes with highly irregular surfaces wherein the defect can be simply shifted to a lower corneal altitude and thus create a new defect which is often unpredictable under the prior art systems. This would be true for both PRK and LASIK treatments as in the former the laser would ablate deeper into the eye then what was originally contemplated in any valley area in the topography of the eye and not as deep as expected in any peak or protrusion area of the topography. With LASIK, the microkeratome is designed to remove a constant thickness flap by way of pressing down during the cutting or planarization process such that the topography of the external surface of the cornea is duplicated in the exposed corneal stroma therebelow.

Because the prior art systems rely on rigid patterns and formulas that are based on standard optical models, they limit the surgeon from fully exercising his clinical expertise during the determination of an ablation profile to be performed. In other words, they do not allow a surgeon to customize an ablation profile to best suit the surgeon's clinical evaluation of the patients corrective requirements.

The prior art systems are also not well suited for many eye corrections that require fine detail or customized ablations particularly eye correction cases such as trauma, some congenital defects, and defects that arise due to accidents during eye surgery.

The following articles, patents and patent application provide additional background information and are incorporated herein by reference:

U.S. Pat. No. 4,721,370 (L'Esperance); U.S. Pat. No. 4,995,716 (Warnicki et al.); U.S. Pat. No. 5,133,726 (Ruiz et al.); U.S. Pat. No. 5,159,361 (Cambier et al.); U.S. Pat. No. 5,318,046 (Rozakis); U.S. Pat. No. 5,533,997 (Ruiz et al.) and U.S. Pat. No. 5,843,010 (Cambier et al.) and pending U.S. patent application No. 09/186,884 (now U.S. Pat. No. 6,302,877) to Luis A. Ruiz.

"Corneal Topography—The state of the Art" James P. Gill et.al. Published by Slack Incorporated.
  Chapter 3. "Characterizing Astigmatism: Keratometric Measurements Do Not Always Accurately Reflect Corneal Topography." 25–33.
  Chapter 5. Thornton, Spencer P. and Joseph Wakil. "The EyeSys 2000 Corneal Analysis System." 55–75.
  Chapter 7. Snook, Richard K. "Pachymetry and True Topography Using the ORBSCAN System." 89–103.
  Chapter 9. Smolek, Michael K. and Stephen D. Klyce. "The Tomey Technology/Computed Anatomy TMS-1 Videokeratoscope." 123–48.
  Chapter 16. Durrie, Daniel S., Donald R. Sanders, D. James Schumer, Manus C. Kraff, Robert T. Spector, and David Gubman. "Evaluating Excimer Laser Procedures." 241–61.
Ren, Qiushi, Richard H. Keates, Richard A. Hill, and Michael W. Berns. "Laser Refractive Surgery: A Review and Current Status." *Optical Engineering*, 34, 642–59 (1995).
Lin, J. T. "Critical Review on Refractive Surgical Lasers." *Optical Engineering*, 34, 668–75 (1995).
Munnerlyn, Charles R., Stephen J. Koons and John Marshall. "Photorefractive Keratectomy: A Technique for Laser Refractive Surgery." *J. Cataract Refract. Surg.* 14, 46–52 (Jan. 1988).
Manns, Fabrice, Jui-Hui Shen, Per Soderberg, Takaaki Matsui, and Jean-Marie Parel. "Development of an Algorithm for Corneal Reshaping With a Scanning Laser Beam." *Applied Optics*, 34, 4600–08 (July 1995).

SUMMARY OF THE INVENTION

The present invention is directed at a system and method for corrective eye surgery that allows a surgeon to use his surgical expertise and familiarity with a patient's individual requirements to design an ablation profile that is well suited for the situation. The present invention thus provides the surgeon with an extremely versatile tool which opens up to the surgeon a wide variety of surgical procedure options and thus enables the surgeon to customize each surgery to achieve what is considered under the circumstances to be the best clinical surgical procedure for that patient. In providing a highly customizable system, the present invention avoids restricting the surgeon to rigid ablation profiles which in some instances only lead to additional defects or fail to substantially improve the vision of the patient. Under the present invention the surgeon is able to direct the laser beam to produce the specific laser pattern deemed best suited for removing the tissue of the eye to achieve the best clinical result contemplated by the surgeon.

In addition, the present invention provides a highly accurate system that takes into consideration the topographical corneal surface irregularities that vary from patient to patient when performing any one of a wide variety of corneal curvature corrections. By taking the individual's specific corneal topography into consideration there is better avoided the possibility at the post operative state of having remaining corneal topographical irregularities adversely altering the desired results of the surgery. Also, because the surgeon is able to negate the topographical irregularities from patient to patient a more precise and regularized result ensues from patient to patient.

The present invention also features a method and apparatus for calibrating or visualizing the performance of a laser beam in carrying out a laser beam ablation profile which includes the use of a substrate which presents different visual color cues as to what levels the laser beam will reach in carrying out the laser beam profile fed to the laser control system.

The present invention comprises a topographical device that is able to provide data characteristics of a corneal surface topography. Preferably the topographical device is an elevational topographic device that provides data characteristics as to the topography map of a patient's external corneal contour in the form of an elevation map which is represented by a sufficient amount of elevational points with respect to an X-Y plane to provide an accurate representation of the actual topography of the eye. The data characteristics for the elevational map are then exported to the interface system of the present invention.

The interface system includes a topographer/interface input system that receives the exported data from the topography device. The topographer/interface input system extracts the data (e.g., x,y,z data) from the exported data received from the topographer, and preferably stores that data in the form of a matrix which is easy to process by the data processing system of the interface system.

The data processing system determines a fit reference sphere which can be an averaged or median sphere with respect to the peaks and valleys of the actual topography (e.g, a sphere that has an equal volume of tissue or peaks above the sphere as to the volume of the non-tissue or valley locations therebelow). A variety of techniques can be utilized to form the fit reference sphere such as a recursive spline-subdivision or a Bezier curve technique.

The interface system includes a visualization system linked to the data processing system so that, based on data fed from the data processing system, the visualization system provides a plurality of visual and interactive screens which enables a surgeon to manipulate and customize ablation profiles to achieve a particular profile that is considered by the surgeon to be the best ablation profile for that particular patient. With the data processing/visualization systems combination of the present invention the surgeon is able to view a variety of different ablation profiles which are considered possible solutions and is able to view simulated post operative views of each proposed ablation profile.

The data processing system includes a reference section or module that processes data concerning the interrelationship between the topographical contour determined by the topographer device and received by the interface system and a reference means such as the previously determined fit reference sphere. With the stored elevation data (e.g. a data matrix for both the actual contour and the fit reference sphere) two and/or three dimensional visual depictions are provided along any one of a plurality of possible eye axes for both the actual topography configuration and the fit reference sphere. The fit reference sphere is presented in a two dimensional view window of the visualization system as a straight line that is initially below (when a median fit reference sphere is chosen as the initial reference) the uppermost elevations of the topography profile shown in two dimensional form. This two dimensional representation of the fit reference sphere can be used as a starting or reference point for the surgeon to begin manipulating and viewing different ablation profiles required to remove the tissue from the topography contour down to the fit reference sphere. The interface system provides means for varying the relative position of the fit reference sphere with respect to the actual topographical contour. The variation between the two is preferably represented by a shifting of the height of the straight line representing the fit reference sphere within a two dimensional grid while the two dimensional profile configuration of the actual topography contour (taken along that same axis) stays fixed on that grid. At the same time, a plurality of screens show how the ablation profile and a simulated post operative eye contour would look upon each shift in position of the reference line (e.g., shifts along a one diopter elevational scale). The ablation profile and resultant eye contour configuration is preferably shown both in a two dimensional grid and a three dimensional depiction with the three dimensional depiction preferably being a topographical color depiction as to the diopter deviation for the eye contour and ablation profile across the cornea surface of the eye. The surgeon can thus determine the simulated effect on the overall resultant eye profile and the configuration and depth of the ablation profile required to achieve that final contour when a certain reference plane is utilized.

For example, the surgeon may shift the fit reference sphere down with respect to the actual eye topography representation which would appear in the two dimensional view screen as a lowering of the reference line with respect to the eye's two dimensional topography profile taken along a common, predetermined eye axes. If, for example, the surgeon was to shift the reference line down to a height which corresponded to the deepest most point of the topography profile, the surgeon would be able to determine the maximum ablation depth required to carry out a correction that removed all topographical deviations at least along the axis being viewed. In certain situations, however, such as where there is a localized, very deep valley in the topography of the eye, there would be required too deep and/or large a volume of ablation such as where there is not much corneal stroma depth to work with (a post operative correction of an accident occurring in an earlier surgery). Accordingly the setting of the reference line to conform to the lowest topographical point in the surface of the eye may not be well suited for that patient despite that ablation profile being the best suited for removing all irregularities in the eye's topographical contour.

It is here that the examiner can use his surgical expertise and familiarity with the patient to shift up the reference line to a location that presents the best clinical ablation profile under the circumstances. For example, the surgeon may shift the reference line a few diopters up (e.g., 5 diopters up) so as to remove a large percentage of any eye irregularities up above the reference sphere while avoiding any perceived problems with over ablation. The present invention makes it easy for the operator to determine when a potential problem may exist. For instance, a particular color can be assigned to any ablation depth that would involve having to go beyond a lower range point (e.g. 0.170 mm depth) whereby the view screen would provide a ready recognizable warning as to a potential problem. A separate screen pop up box with a question as to whether such a profile is desirable can also be provided. Situations might also arise where it is deemed better not to use the deepest valley point as the basis for picking the elevation of the proposed best clinical sphere on the basis that it would be more clinically desirable to take less volume off by shifting the proposed best clinical sphere up in elevation and relying on a more localized custom formula technique directed at negating any remaining aberration(s) remaining below the chosen best clinical reference sphere.

Together with the two dimensional view screen showing the reference line and topography profile interrelationship, there is preferably provided a sliding elevation deviation button and scale representation which can be computer mouse controlled to easily vary the height of the reference line with respect to the topography profile. A similar sliding scale arranged horizontally to allow an operator to vary the diameter of the proposed best clinical sphere is also preferably provided as well as number indicators as to the radius, curvature and relative position of the best clinical sphere with the fit reference sphere. The surgeon is thus able to easily also change the shape of the proposed best clinical sphere to induce either a flatter curve configuration or a steeper best clinical sphere configuration depending upon the surgeon's clinical evaluation as to what type of curvature is best for correcting the eye without introducing any significant undesirable post operative effects and preferably removing the least amount of tissue required under the circumstances. The number view windows showing the radius value for the fit reference sphere, the diopter value for the fit reference sphere and the depth or elevation between the original position of the fit reference sphere to the presently displayed height position (a lower or superior position) are interrelated so that upon making a change in one category that results in a change in another category, the change is automatically made by the data processing system and the appropriate value displayed in the display area. Since the elevation between the original fit reference sphere and the actual topographical profile is know for each X-Y reference point and since the change in elevation of the proposed best clinical sphere with respect to the fit reference sphere is known for each point as well, there can readily be determined with elevation deviation monitoring means the difference in elevation (and hence the required total ablation) between the topography profile and the proposed best clinical sphere which is often, but not always positioned below the original fit reference sphere. It is the patient's unique topographical contour and general eye shape coupled together with the desired input expertise of the surgeon that determines what is the best clinical sphere for that patient.

The reference section also includes an eye axes option provider which allows an operator to pick and choose which eye axes (typically an option between the N—T (0) axis, the superior/inferior axis (90°), the 45–225° axis and the 135–315° axis. This option is designed for use with the best clinical sphere determination means of the present invention as it allows an operator to visualize simulated post operative results for a proposed best clinical sphere ablation profile along a variety of different axes.

For example, the surgeon may be confronted with a patient having an astigmatic profile along the superior/ inferior axis which is apparent from a display on a base screen of the color differentiated diopter profile of the pre-operative eye. Recognizing this as an axis best suited for an initial best clinical sphere determination the operator can choose the superior/inferior axis upon which to review different relationships between the two dimensional and three dimensional illustrations of the actual topography, initially determined fit reference sphere and proposed best clinical sphere location. This would provide a good indication of the type of ablation profile that would be required to remove the astigmatic irregularity. This eye may also however have a localized very deep depression that does not fall anywhere along the chosen reference axis. If the proposed best clinical sphere profile presented along the inferior/ superior axis is opted for, then this localized depression would be overlooked and remain such that there would remain some visual degradation due to the configuration of the corneal surface. If a check were made along an additional axis such as the 45 degree axis and the very deep localized valley fell along that axis, then the surgeon could make a clinical determination as to whether the best clinical sphere ablation profile should fall at the lowest depth point of the localized valley or whether that would create ablation depth profiles so as to warrant an intermediate best clinical sphere height somewhere above the lowest depth point and below the elevation determined for the superior/inferior axis. Accordingly, the surgeon is able to interact with the present invention to determine the best clinical sphere suited for the particular patient involved through, for example, determining which axis or axes to choose for viewing simulated results based on experience and the initial topography presented as well as determining whether or not a best clinical sphere should be placed at the lowest point on the topography profile or some alternate compromise setting which is deemed clinically more appropriate under the circumstances.

Furthermore, the best clinical sphere ablation profile can either be used alone if the surgeon deems that it is sufficient based on the patient's situation or coupled with additional ablation characteristics. As an example, if a patient has an astigmatic creating configuration which is to be removed with a best clinical sphere setting, but that ablation profile would create at the same time a hyperopic over correction in the eye that situation can be offset by adding additional ablation profile directions to achieve a more myopic resultant eye based on an ablation profile that can be either one that is a standard clinical or "normal" profile or one that is self generated by the surgeon in a customizing step such as by choosing various factors to alter an ablation profile or by choosing a saved profile (including an earlier surgeon self generated file of useable profiles or profiles provided initially with the interface system).

BRIEF DESCRIPTION OF THE PREFERRED DRAWINGS

The file of this patent contains at least one drawing executed in color. Copies of this patent with color drawing(s) will be provided by the Patent and Trademark Office upon request and payment of the necessary fee.

FIG. 1 shows a block' schematic view of the flow of data in the system of the present invention from the patient to the laser system;

FIG. 2 shows a block schematic view of the hardware of the system of the present invention;

FIGS. 5A, 5B and 5C show a flow chart depicting the various processing modules and some of possible routes therebetween provided in a preferred embodiment of the present invention;

Figure 8:
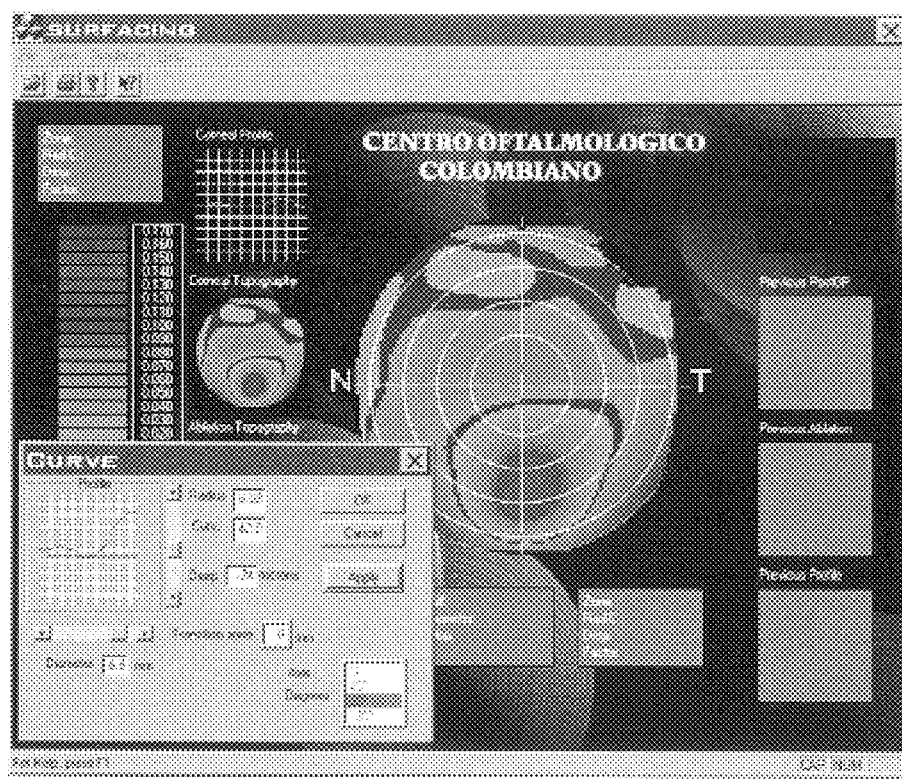
Figure 8A:
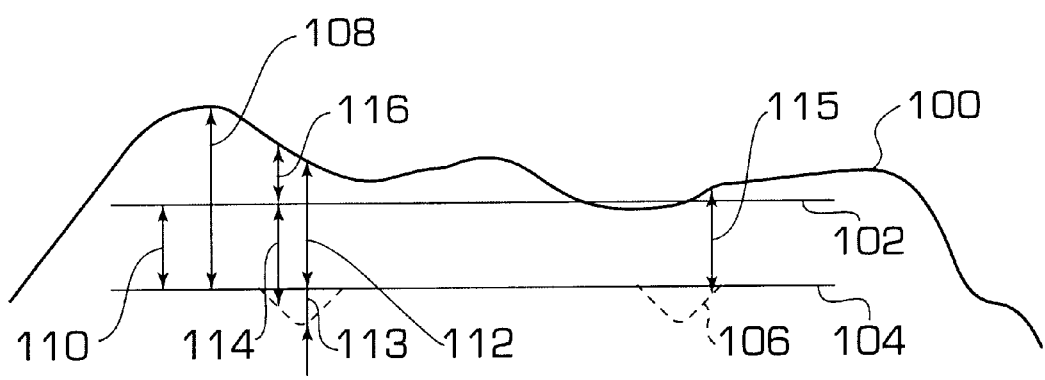
Figure 9:
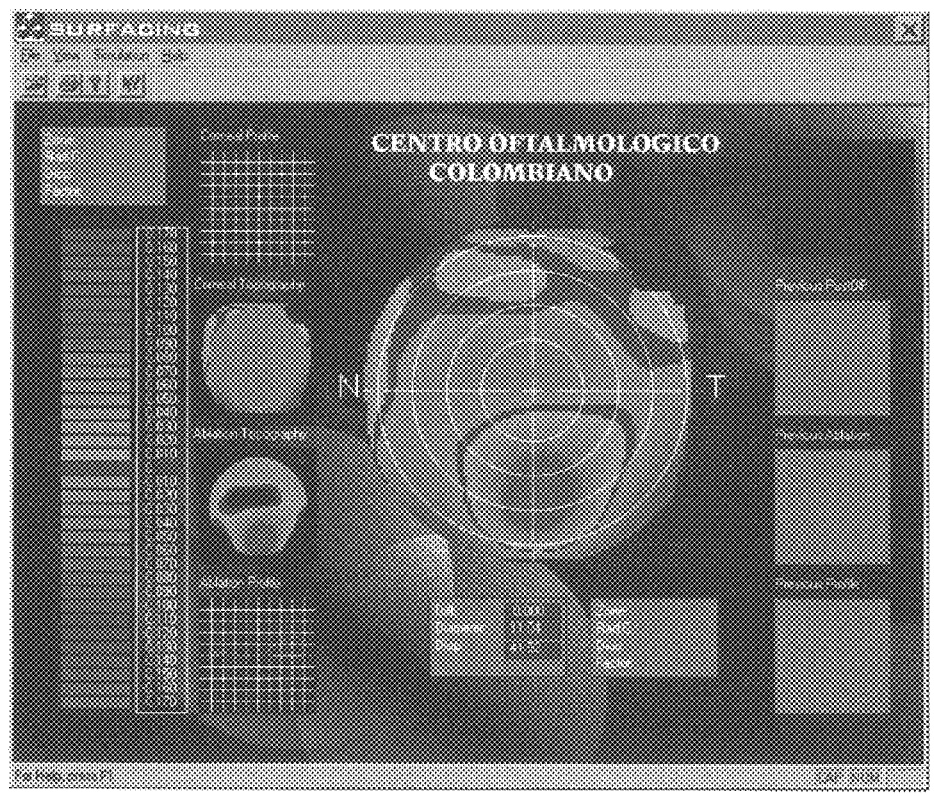
Figure 10:
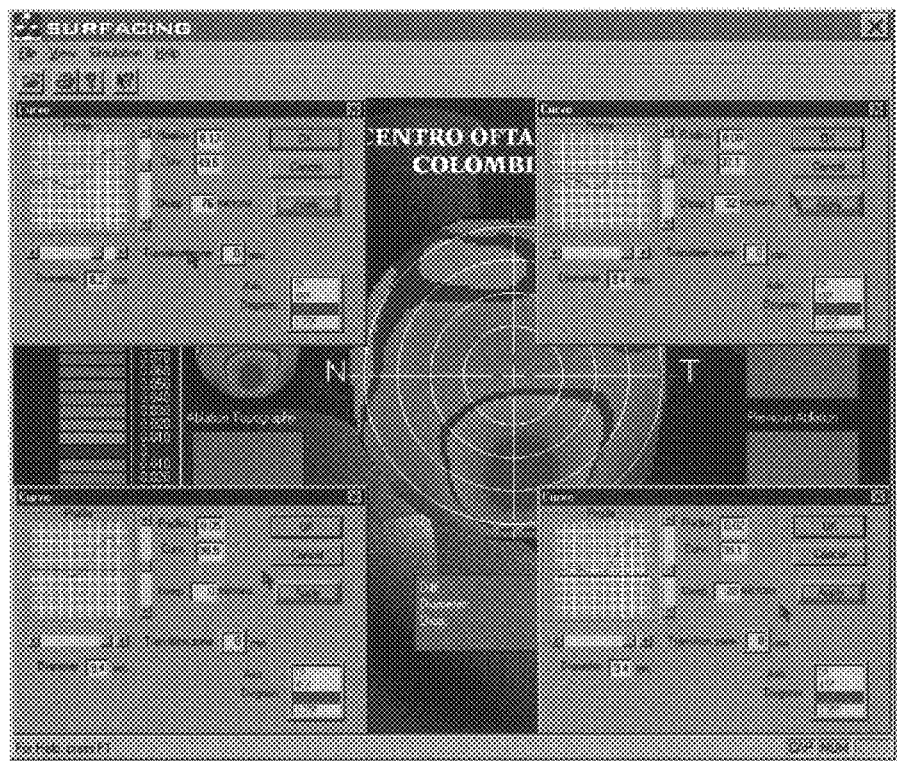
Figure 11:
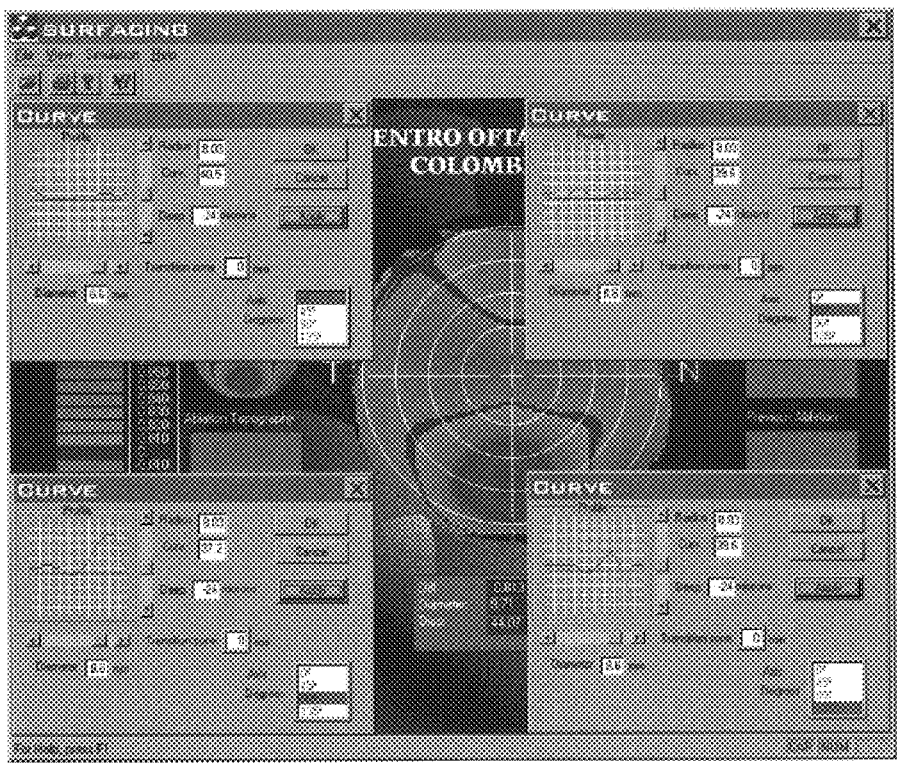
Figure 12:
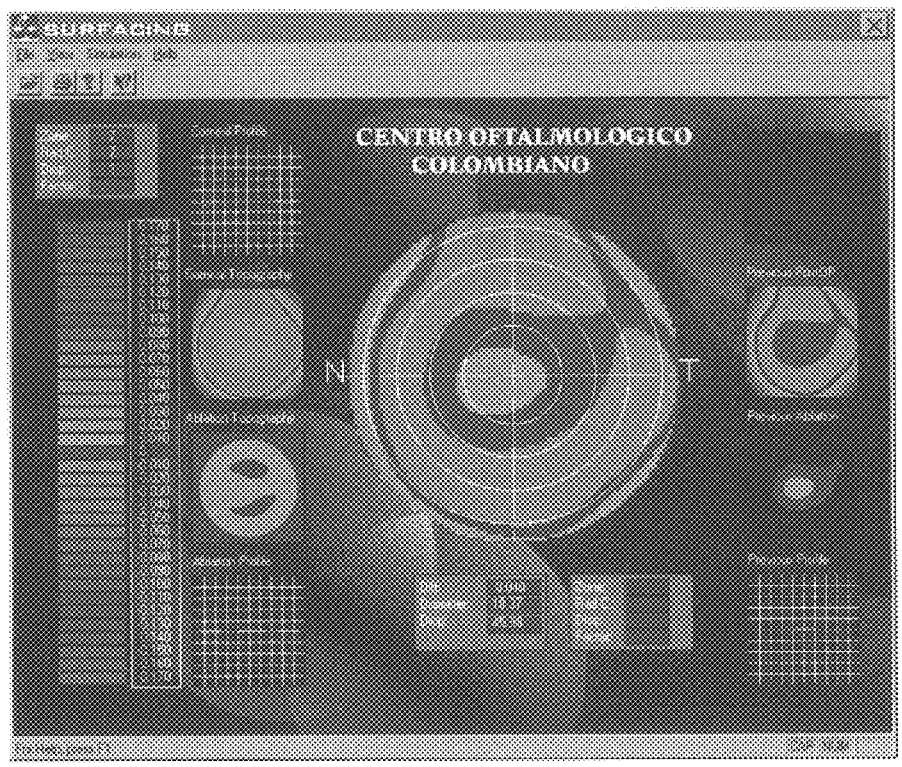
Figure 13:
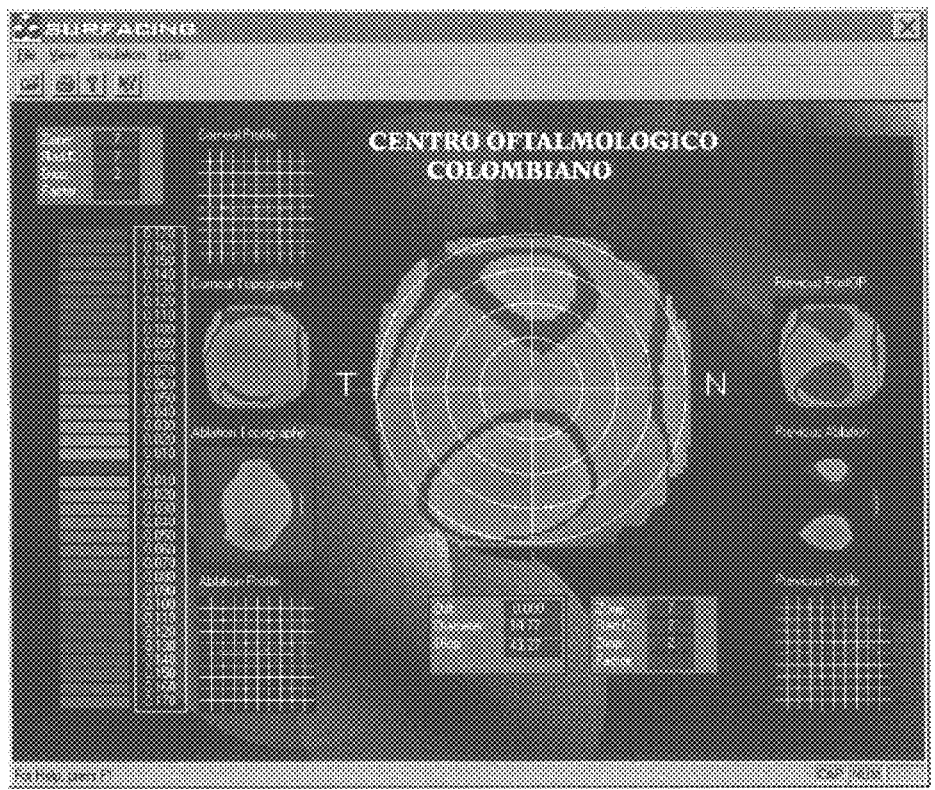
Figure 14:
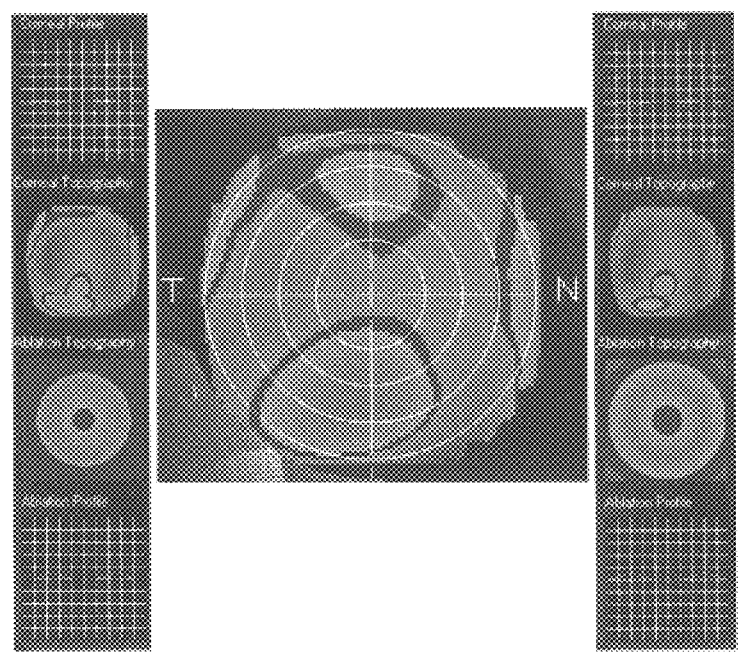
Figure 15:
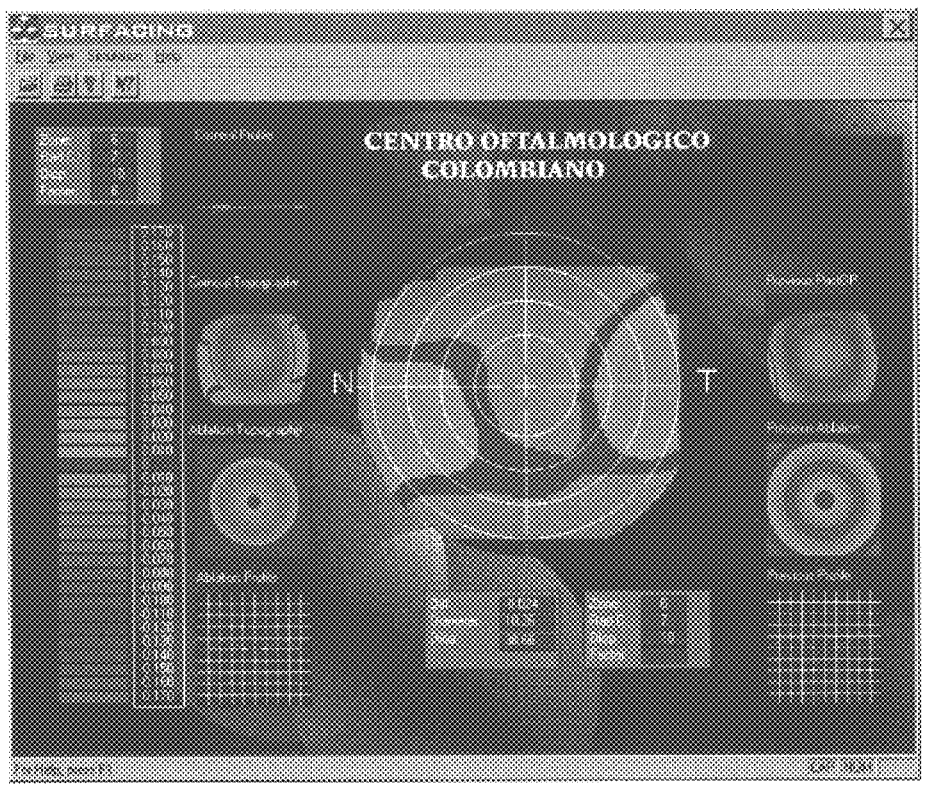
Figure 16:
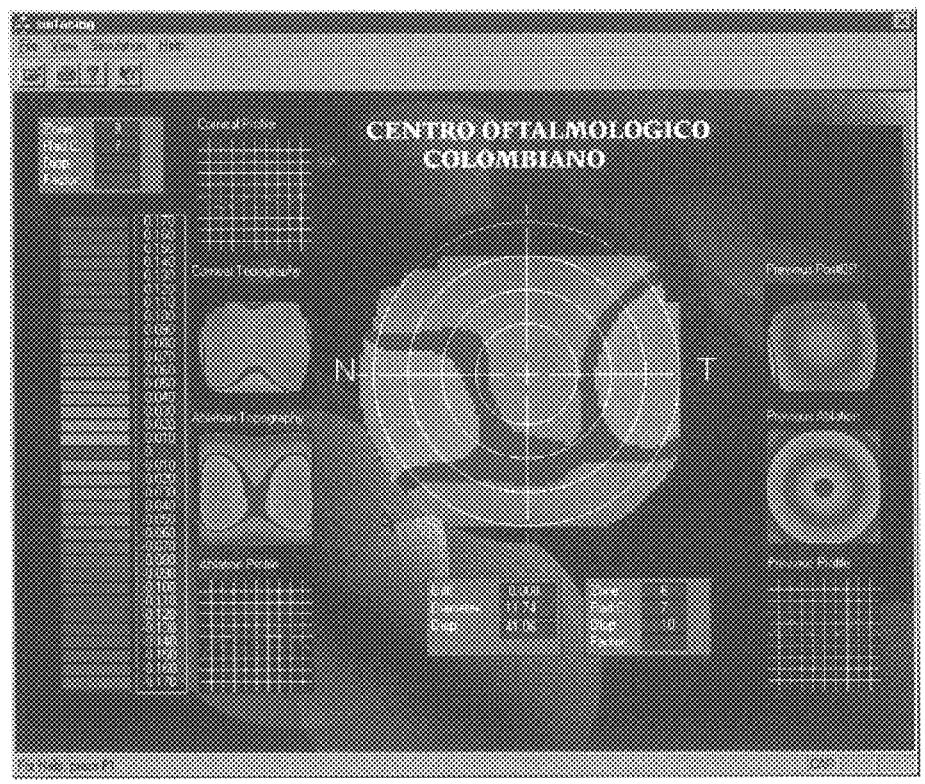
Figure 17:
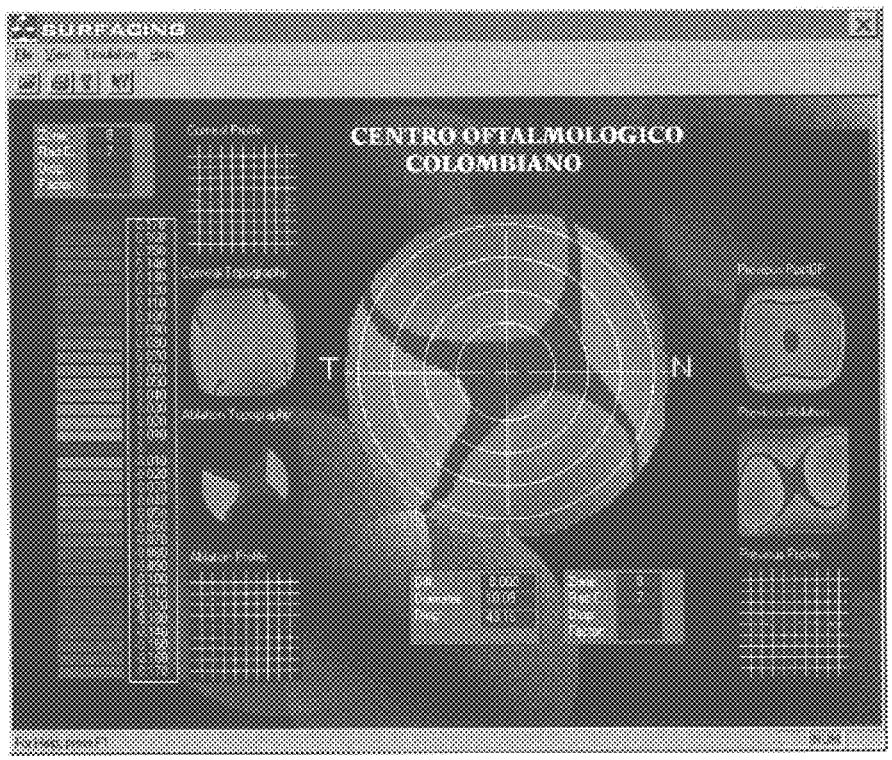
Figure 18A:
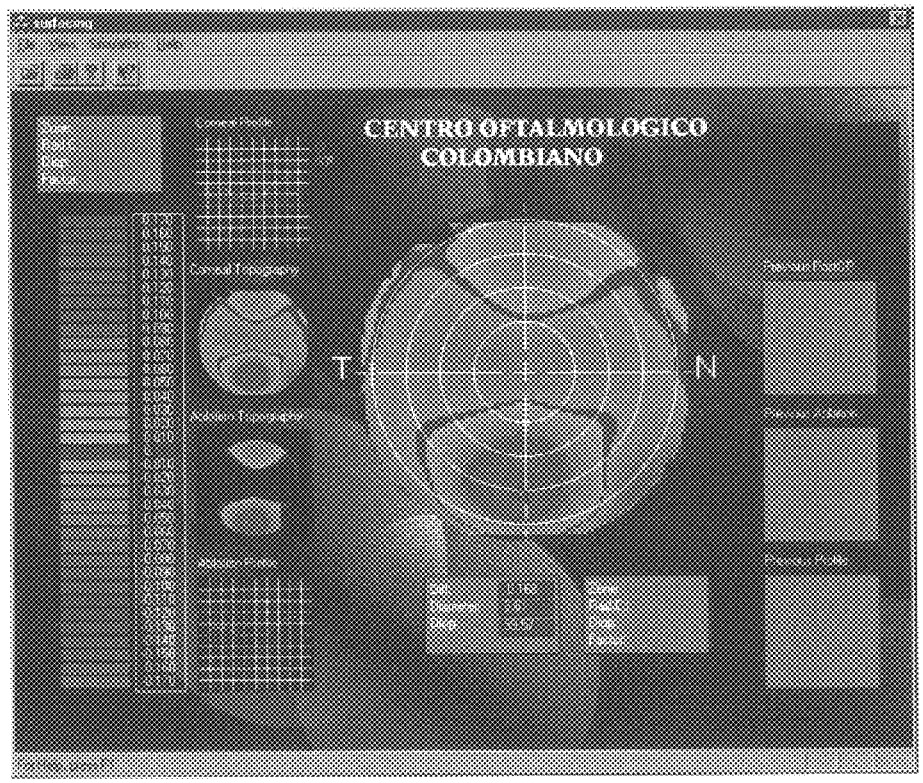
Figure 18B:
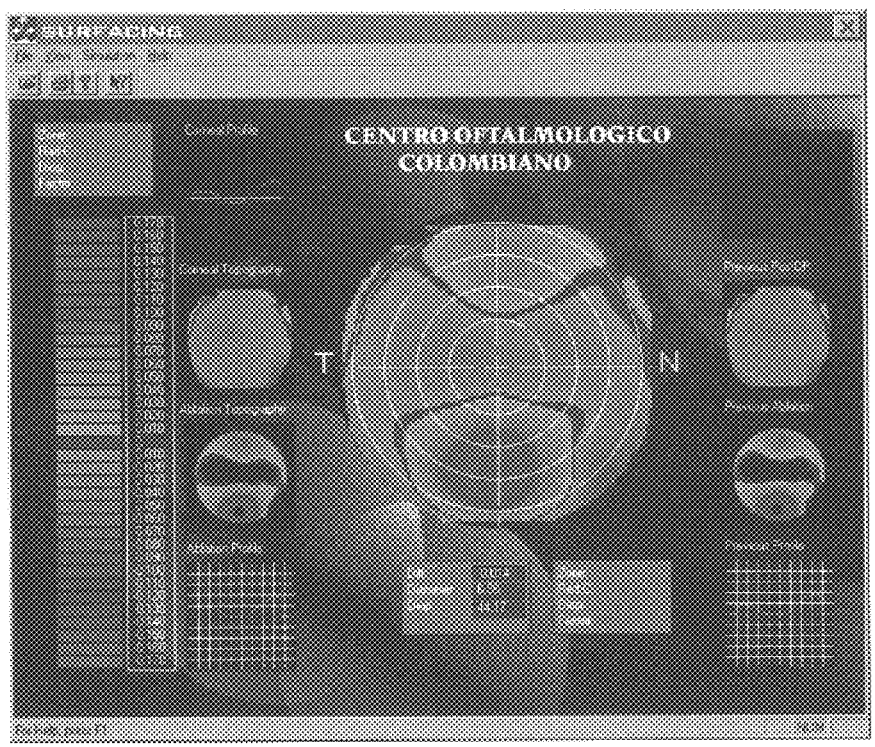
Figure 19:
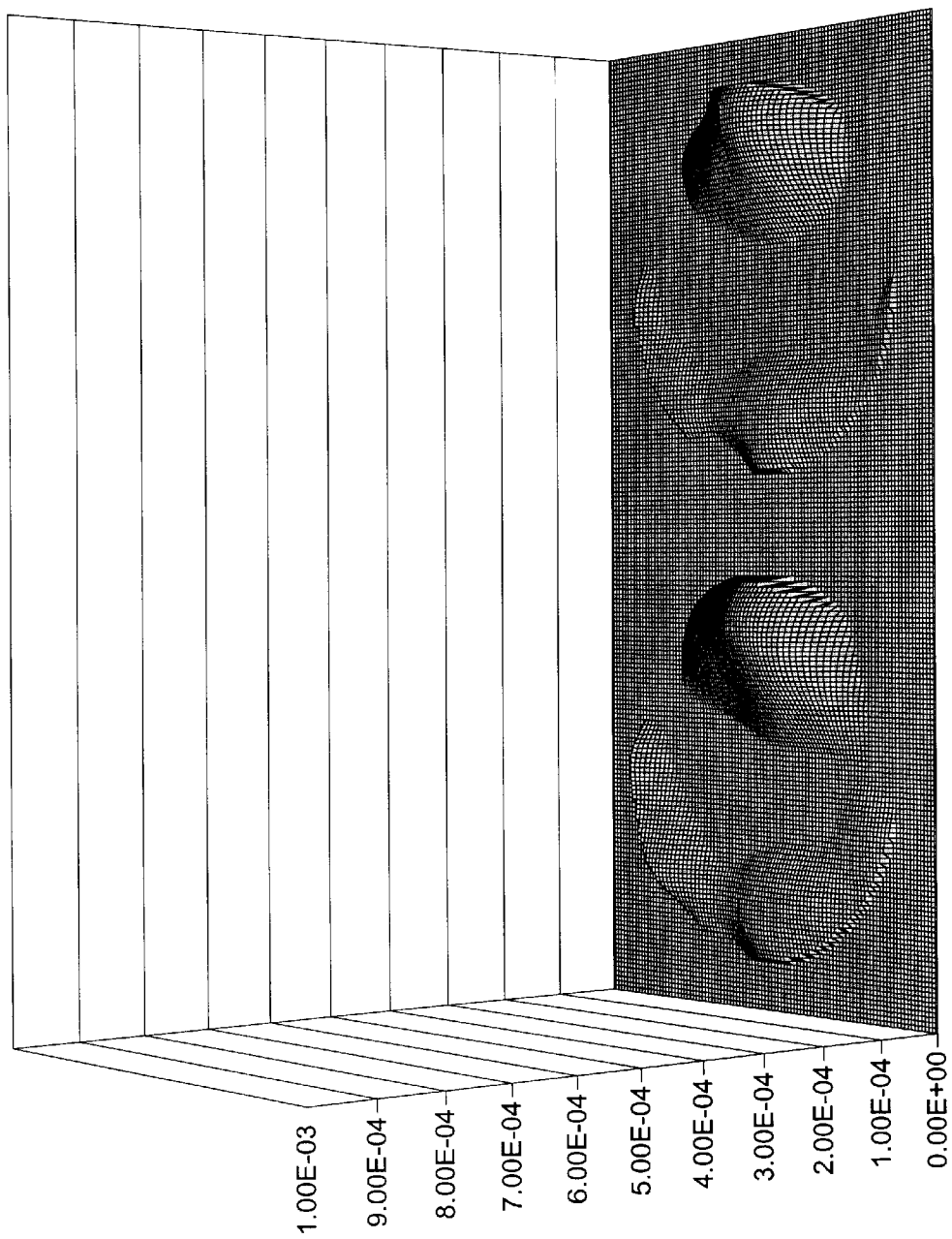
Figure 20:
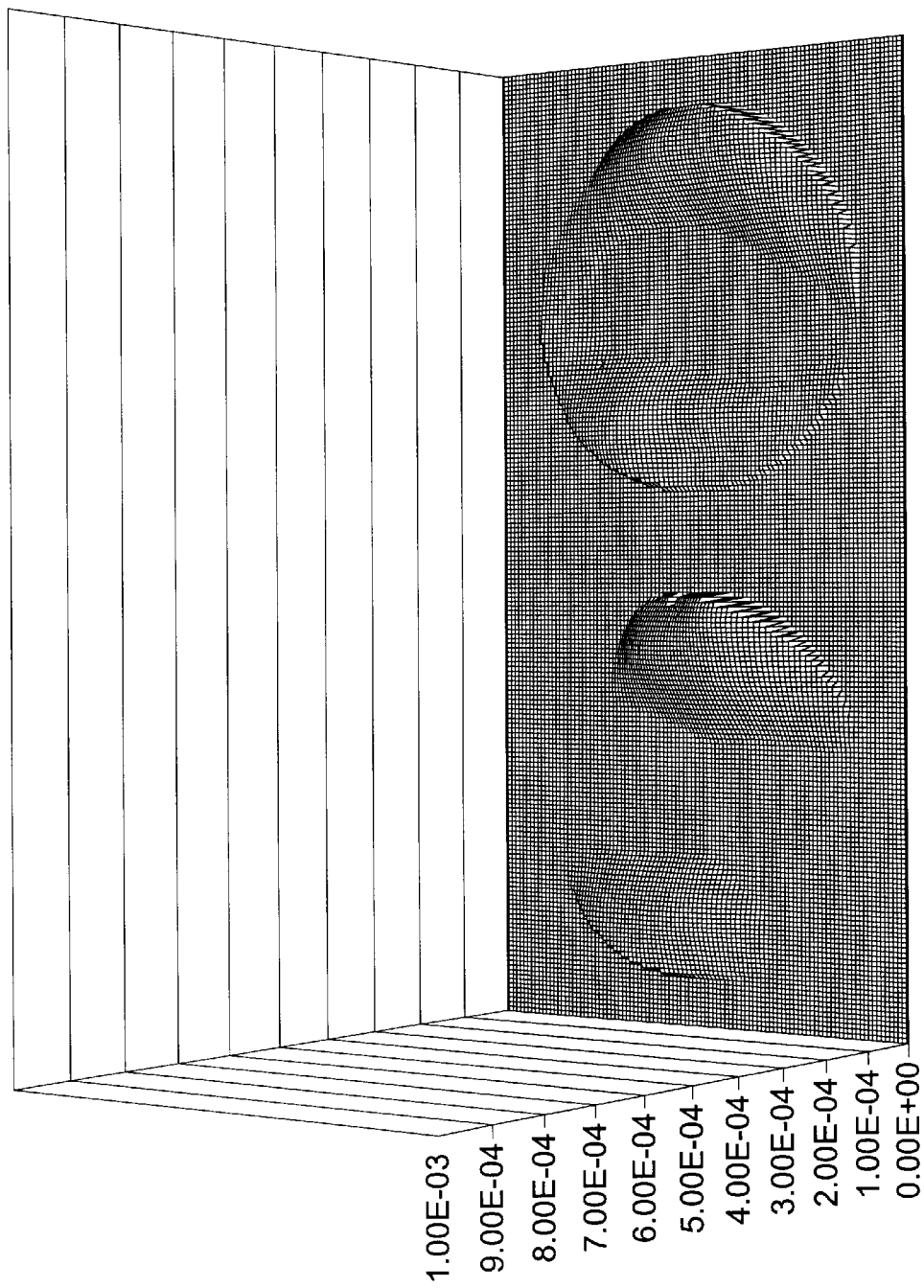
Figure 21:
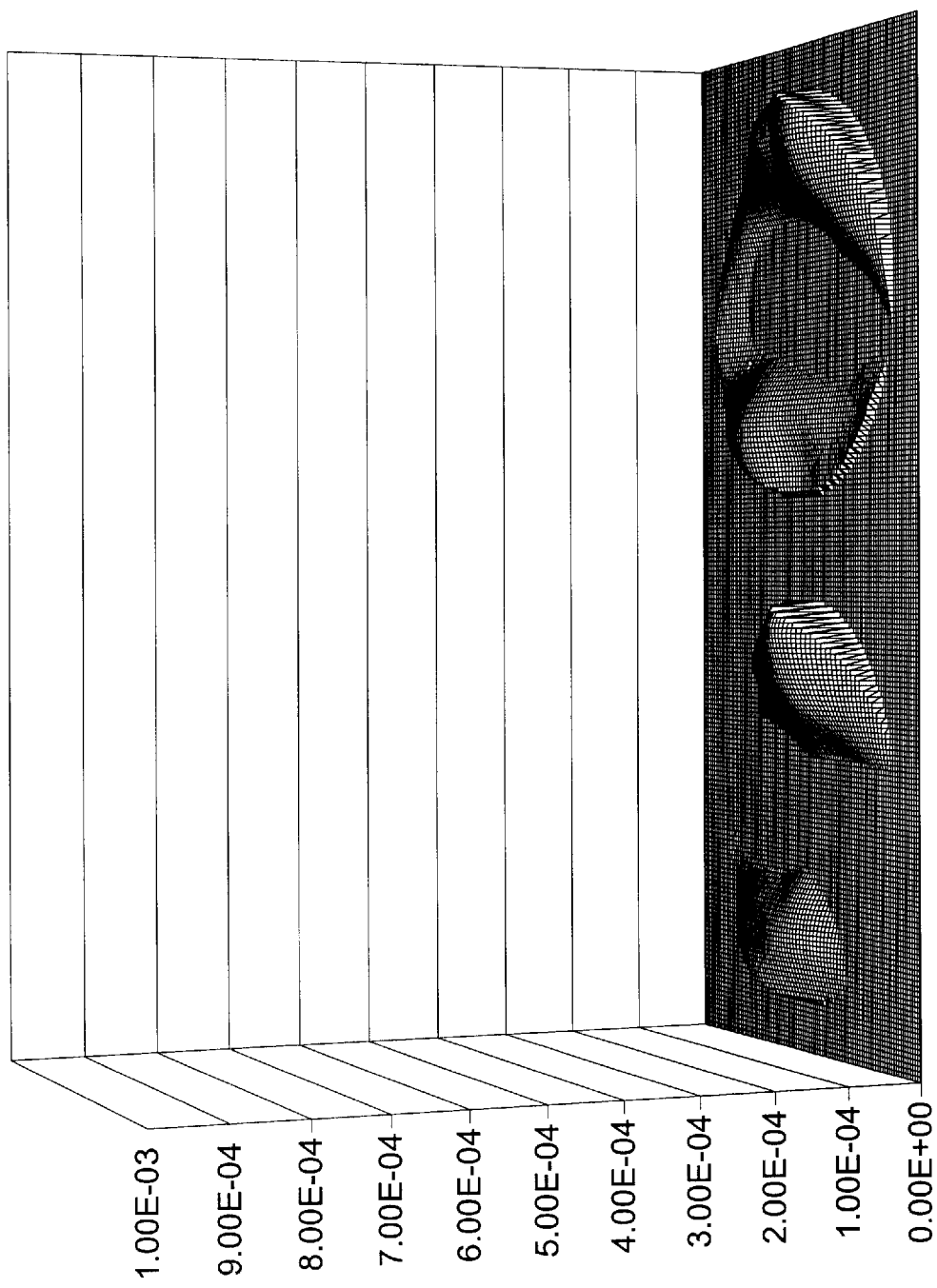
Figure 22A:
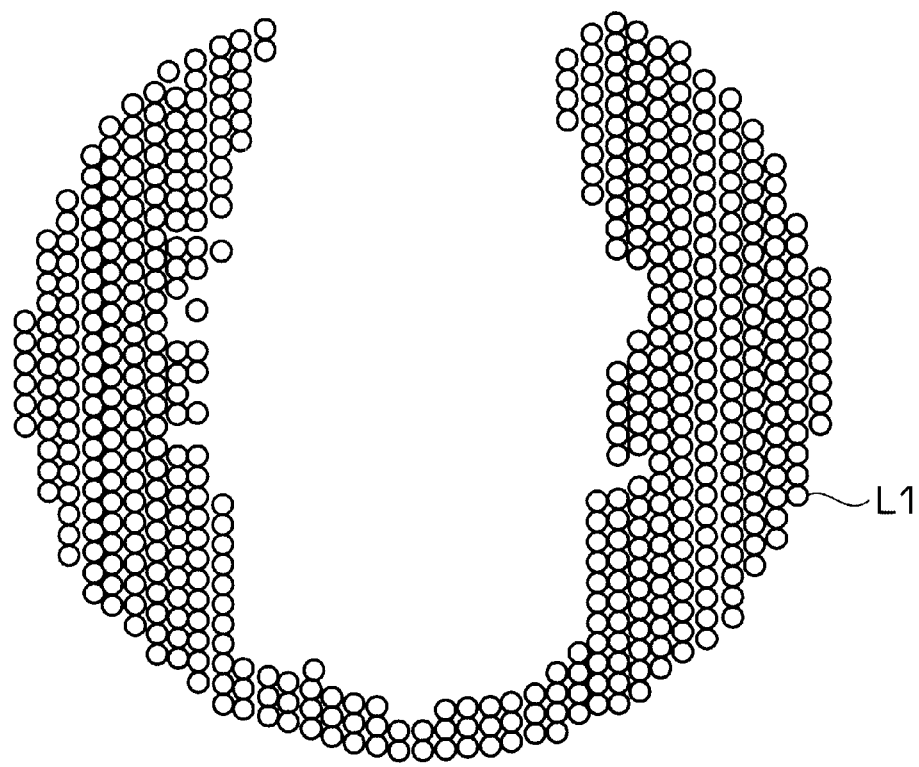
Figure 22B:
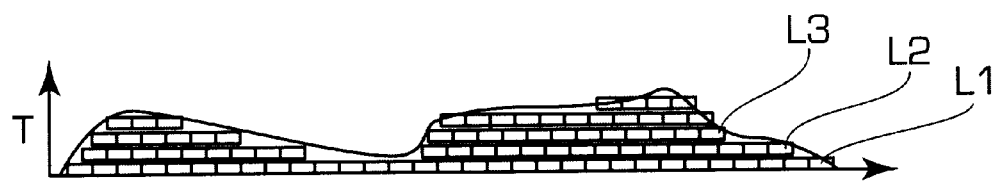
Figure 23A:
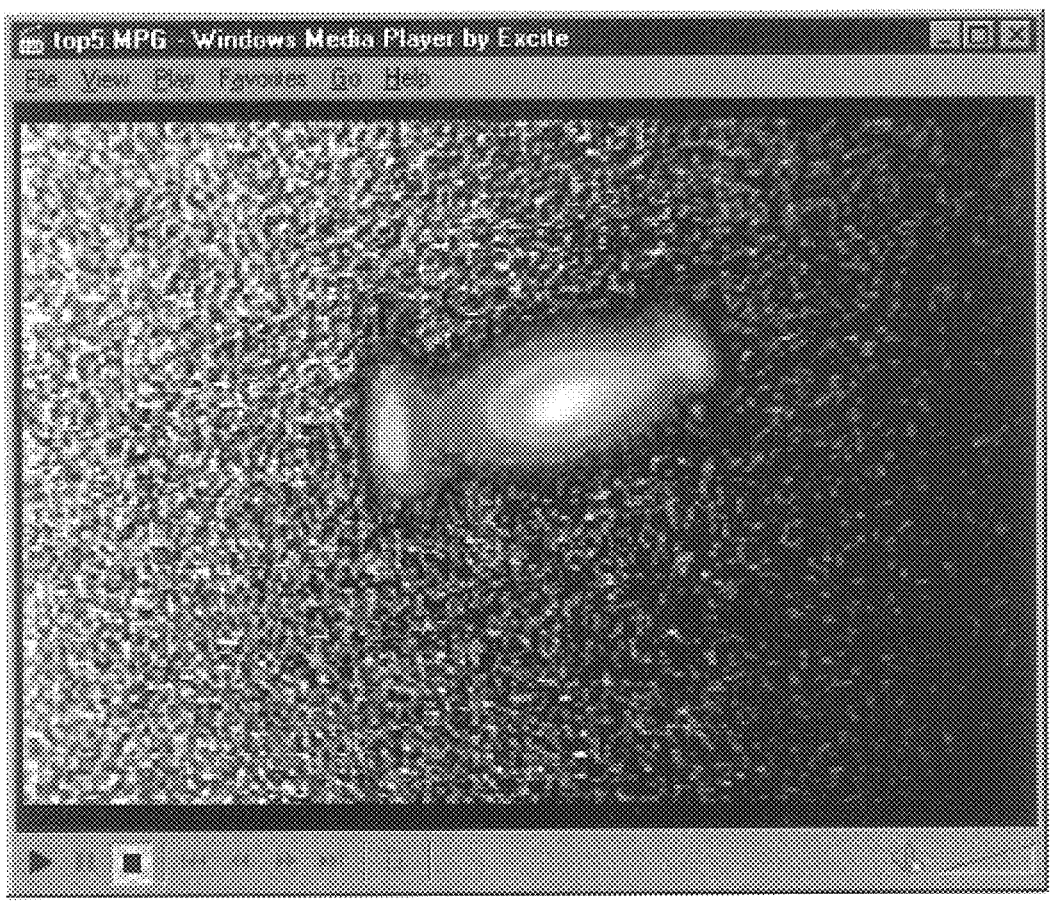
Figure 23B:
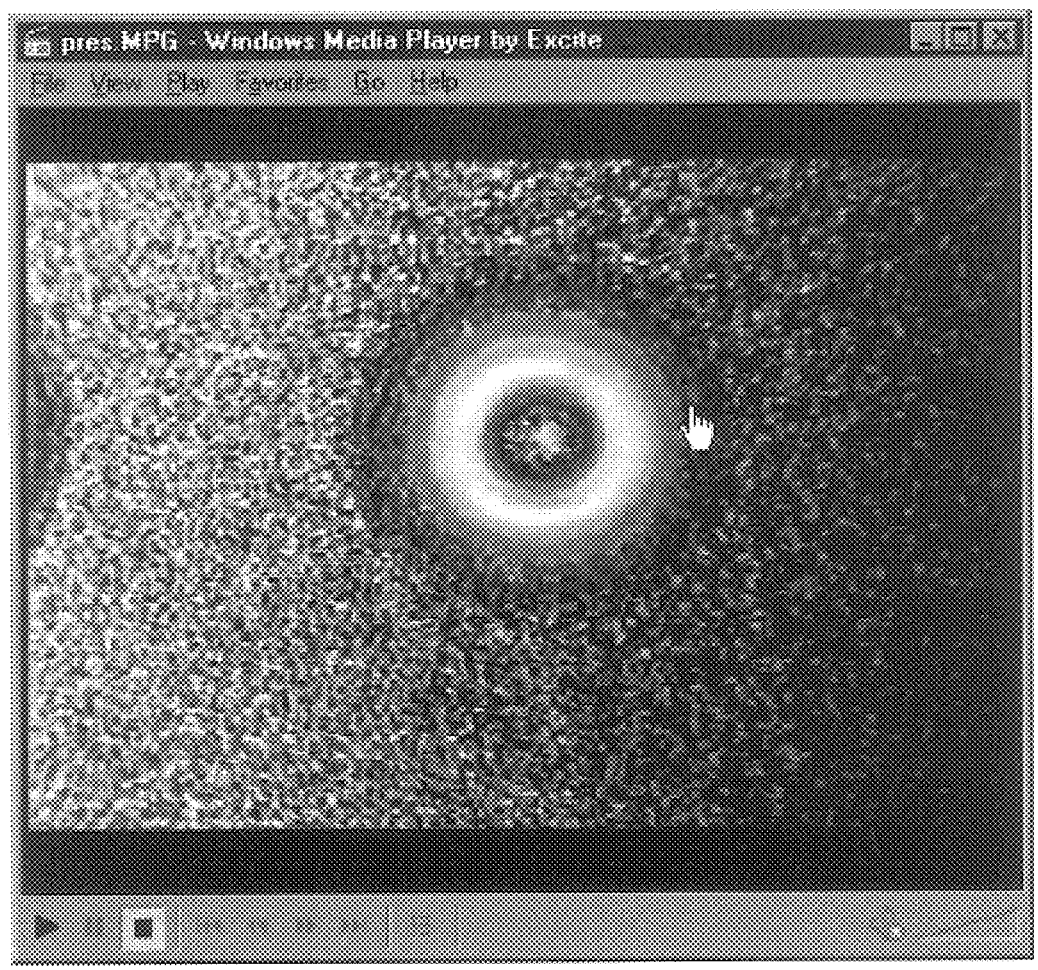
Figure 23C:
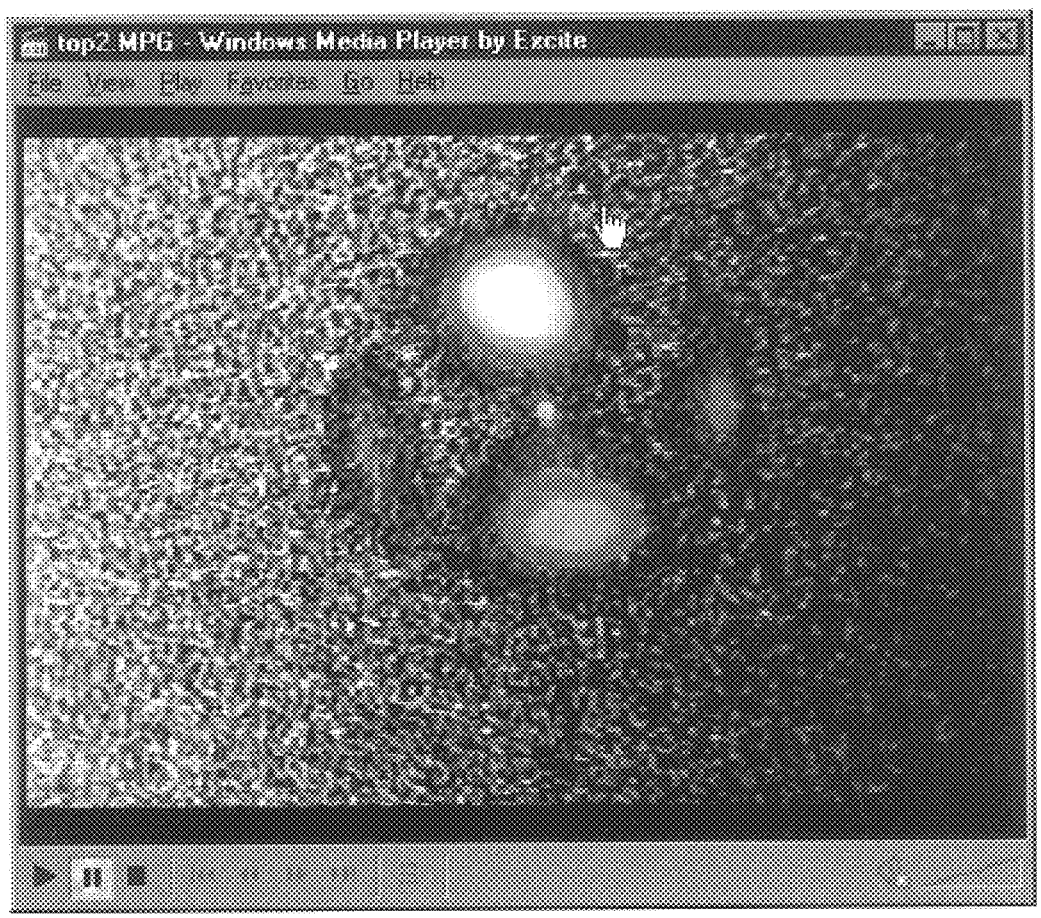
Figure 23D:
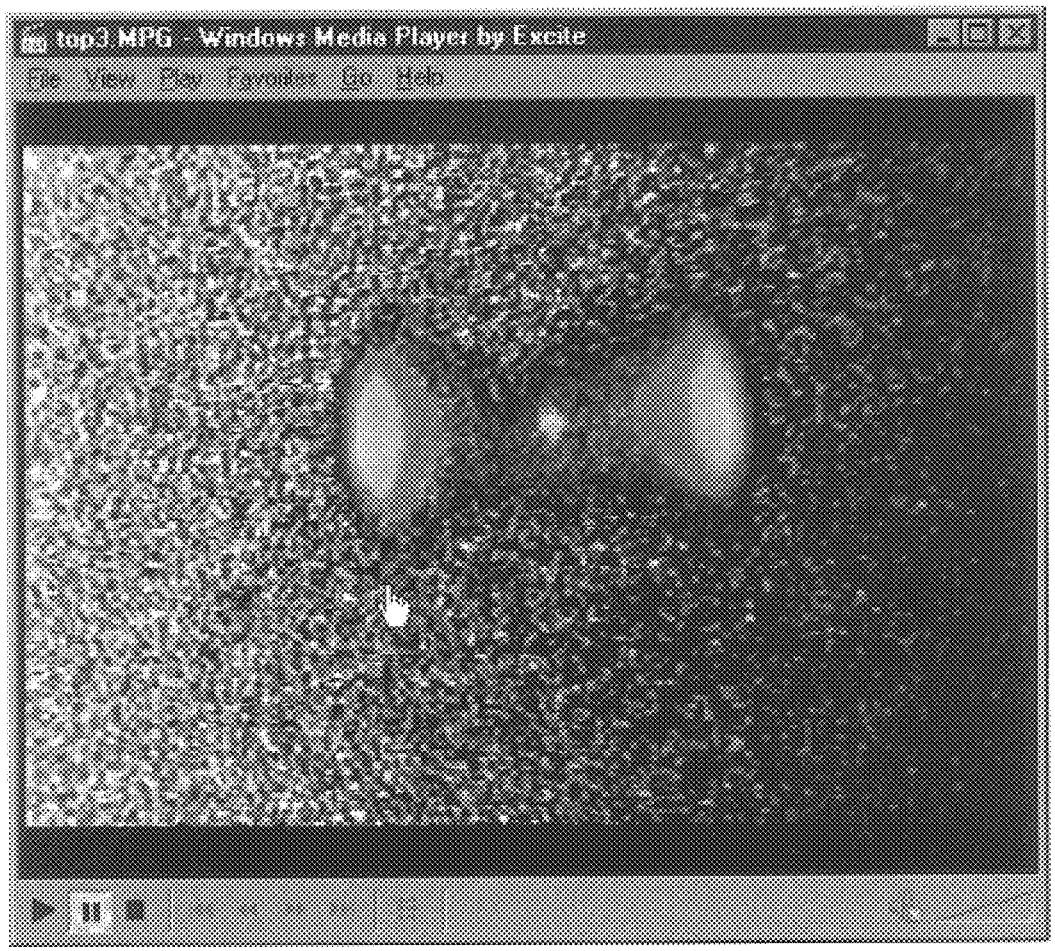
Figure 24:
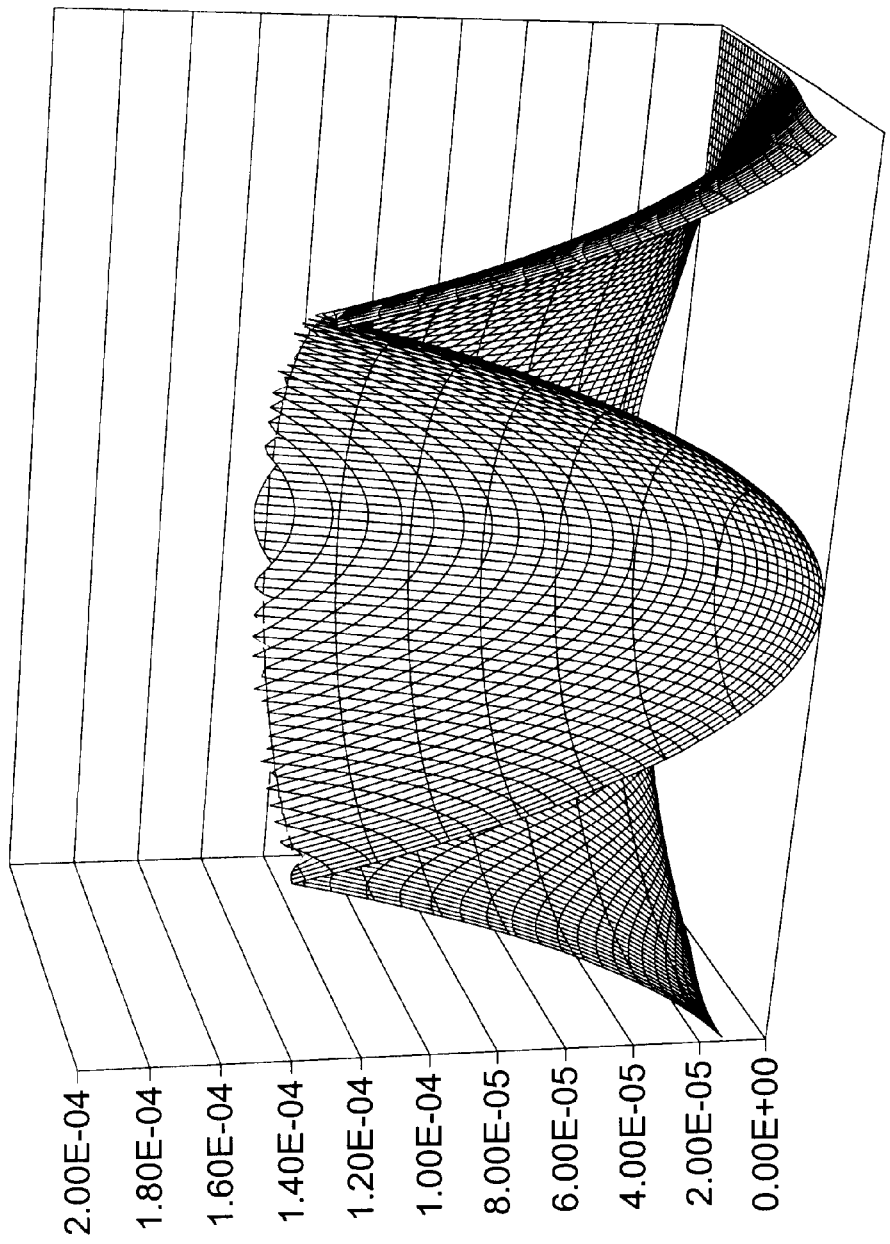
Figure 25:
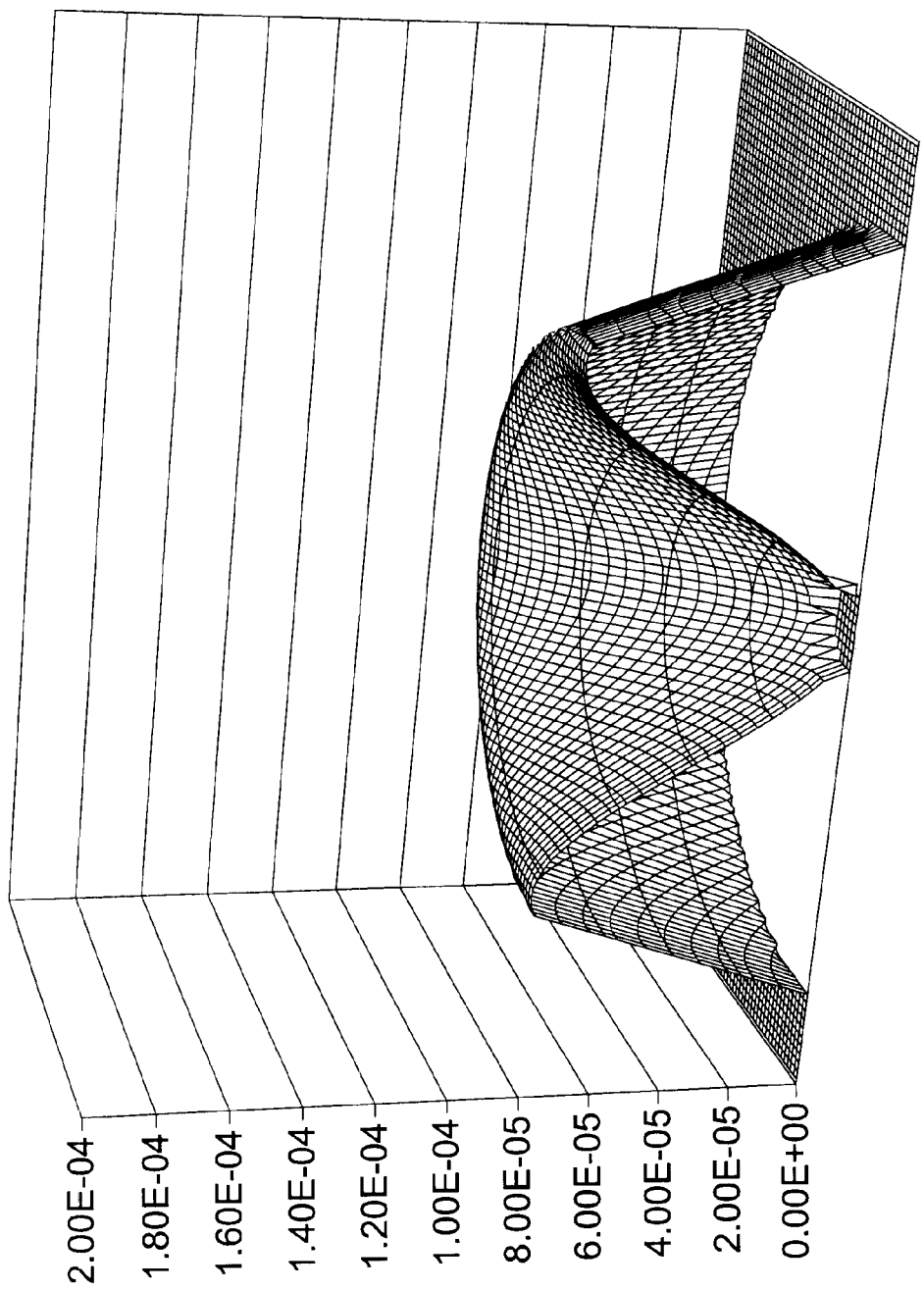
Figure 26:
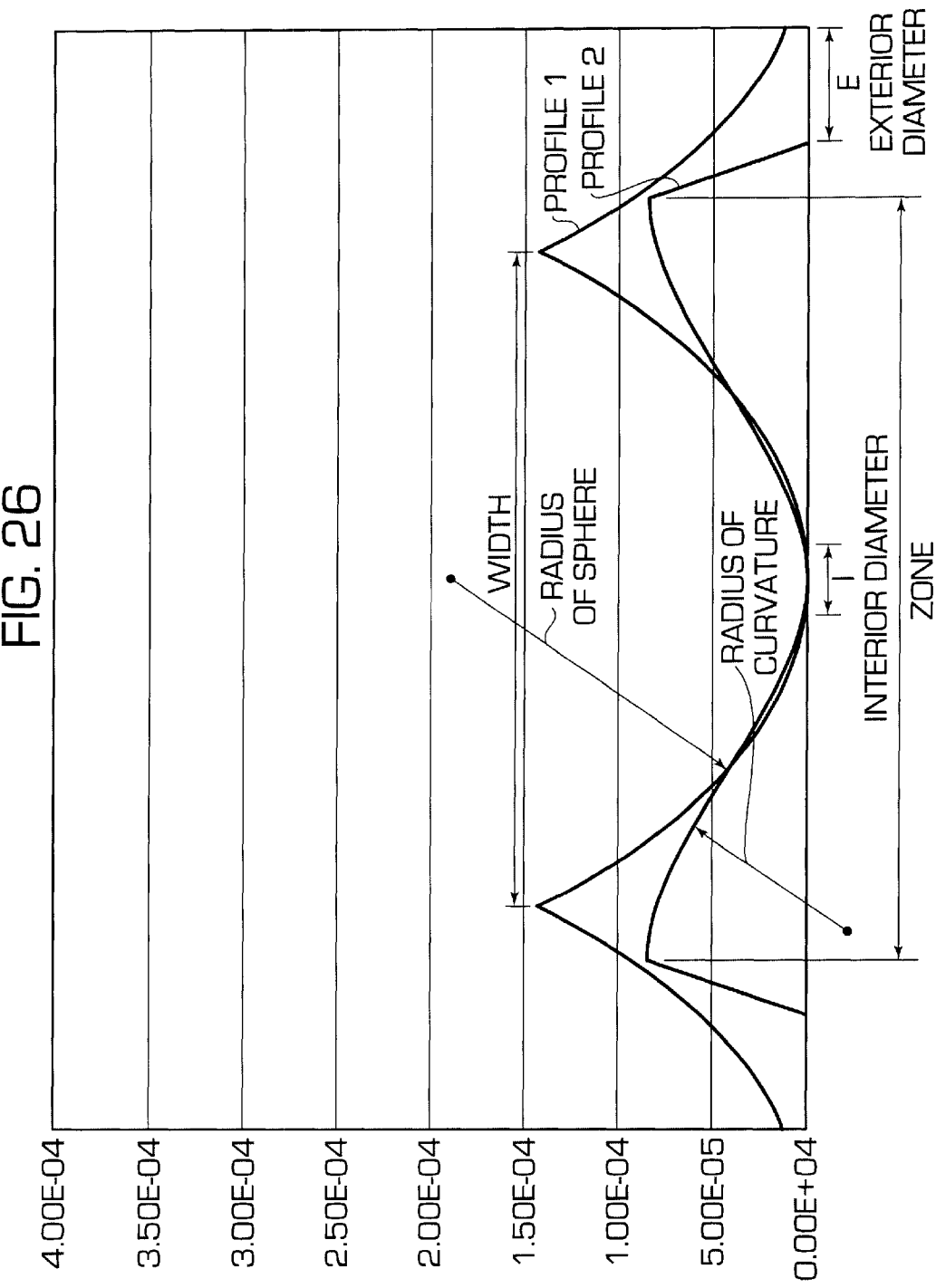
Figure 28:
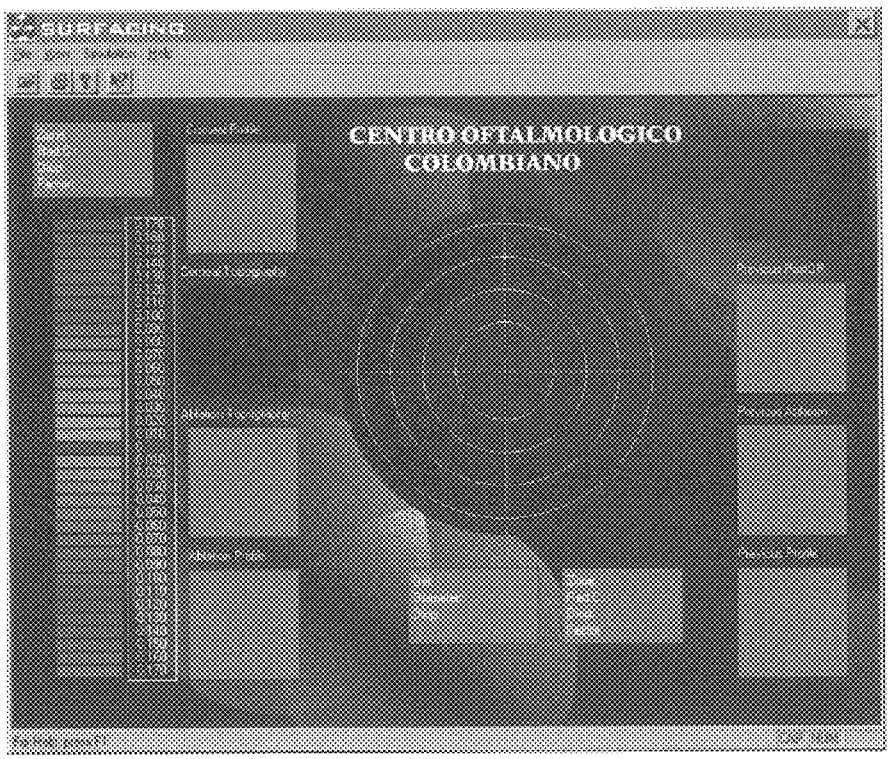

FIG. 8 shows a preferred, main visual screen for the reference module which depicts an irregular eye topography having emphasis along the 90° axis with a sub view overlying window showing a cross section of the cornea profile along that same axis as well as a proposed best clinical sphere location reference ablation line having been moved to a location that results in a diameter of 8.06 mm and a depth of 24 microns with reference to the original fit reference sphere (the original reference line not shown as the line has been moved down to a proposed best clinical ablation location) with such a proposed ablation profile designating a desired post operative curvature radius of 8.03 mm and a refraction of 39.5 diopters;

FIG. 8A illustrates a two dimensional profile along a single axis of the cornea's topography, the two dimensional depiction of the fit reference sphere, the two dimensional depiction of a lower shifted proposed best clinical sphere, and the profile of an additional removal of tissue in a combination reference/hyperopic correction situation;

FIG. 9 shows the same visual screen as in FIG. 8 except with the proposed best clinical sphere ablation profile having been performed in simulation with the ablation profile being implemented and the simulated post operative results shown in the left hand sub screen sections;

FIG. 10 shows a plurality of pop up windows over the main reference module screen which are similar to that for FIG. 8 except for their depicting of different elevation choices for the reference line showing the proposed location for the proposed best clinical sphere;

FIG. 11 shows a plurality of pop up windows over the main reference module window which show the reference line for the proposed best clinical sphere at a common elevation level with respect to the topography contour, but taken along the different option axes (0,45,90,135°) provided within the reference module;

FIG. 12 shows a combination surgical procedure simulation in the reference module section of the system of the present invention which depicts a combination surgical procedure for astigmatism and a regular hyperopic profile that is needed because the highly irregular central astigmatism correction will induce hyperopia due to the flattening of the cornea not needed for this patient thus requiring a hyperopia compensation for the steepening of the cornea back again to its original shape with the right side showing the simulated reference ablation results for the astigmatic correction and the left side showing the combination of the two proposed surgeries;

FIG. 13 shows a combination of a referenced ablation with a regular myopic pattern based on the fact that on the 90 degree axis the correction induces myopia, and shown on the right side is the referenced ablation and on the left side the result of the combined treatment;

FIG. 14 shows the comparison between two myopic treatments of +5 diopters applied over the same eye, with the right side of the visual screen showing a spherical profile and the left side illustrating the same surgery with an aspheric ablation over the same eye;

FIG. 15 shows on the right side of the view screen a spherical ablation profile of +10 diopters and on the left side the same +10 diopters but as an aspherical profile over the same eye, and with there appearing in the bottom the two surgical profiles to make a suitable comparison;

FIG. 16 shows a correction for astigmatism through the simulated interactive astigmatism that is a mathematical alternative to the referenced ablation with the disadvantage being represented that the predicted topographic results are not very regular because the surgery depends largely on the manipulation of the many coefficient factors inside a base equation;

FIG. 17 shows a comparison between a simulated formula based astigmatism procedure on the right side and a simulated reference ablation on the left side;

FIGS. 18A and 18B show main view screens of the opposite (right) eye of the same patient shown in FIG. 9 with FIG. 18A being at one proposed best clinical sphere elevation level and FIG. 18B being at a different elevation level;

FIG. 19 shows two alternate final ablation profiles to achieve two differently positioned proposed best clinical spheres on the same eye with the left best clinical sphere being set about 20 microns lower than the right one;

FIG. 20 shows, for a different patient, similar views as that in FIG. 19 for two proposed best clinical sphere settings at elevations about 20 microns apart;

FIG. 21 shows the same view as in FIG. 20, but with the view having been rotated up for a different perspective view of the ablation profiles which are representative of the elevation coordinates to be fed to a laser system;

FIGS. 22A and 22B show schematic views of the laser's pulse application which is controlled to ablate only those areas of interest as determined by the final ablation profile and is designed to apply randomly directed (to avoid localized heating) pulses to remove layers of tissue of the cornea (the layers often involving different peripheral profiles) which when applied to completion remove the volume of tissue dictated by the chosen ablation profile such as that shown in FIG. 21;

FIGS. 23A,B,C and D show laser calibration results on a substrate (photography paper test sheet shown) of the present invention which has layers of different color material to depict the different levels of laser depth generated by the ablation profile matrix output from the interface system of the present invention;

FIG. 24 shows a partially cut away ablation profile based on a spherical ablation formula wherein the shape of the central concave portion is governed by a surgeon imputed radius of a sphere and a width or zone or opening of the central concavity of the ablation profile;

FIG. 25 shows a partially cut away ablation profile based on an aspherical ablation formula (multi-curved interior side wall for the ablation contour) wherein the final shape of the aspherical ablation profile is determined by surgeon imputed values;

FIG. 26 shows a comparison between an aspherical ablation profile like that shown in FIG. 25 and a spherical ablation profile like that shown in FIG. 24;

FIGS. 27A to H show a variety of different potential astigmatic ablation profiles that can be used as a reference source for a surgeon to quickly craft a clinical approach to a plurality of different astigmatic profiles together with an illustration of the associated, surgeon variable formula;

FIG. 28 shows an open main window of the "surfacing" file.

Figure 29:
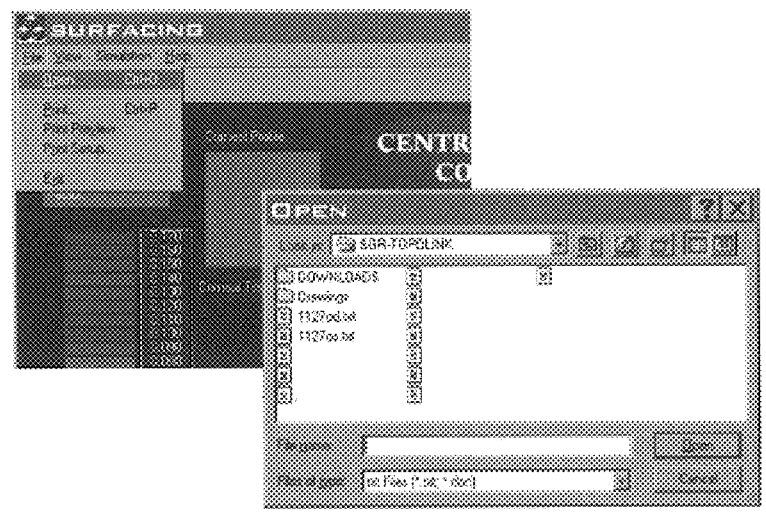
Figure 30:
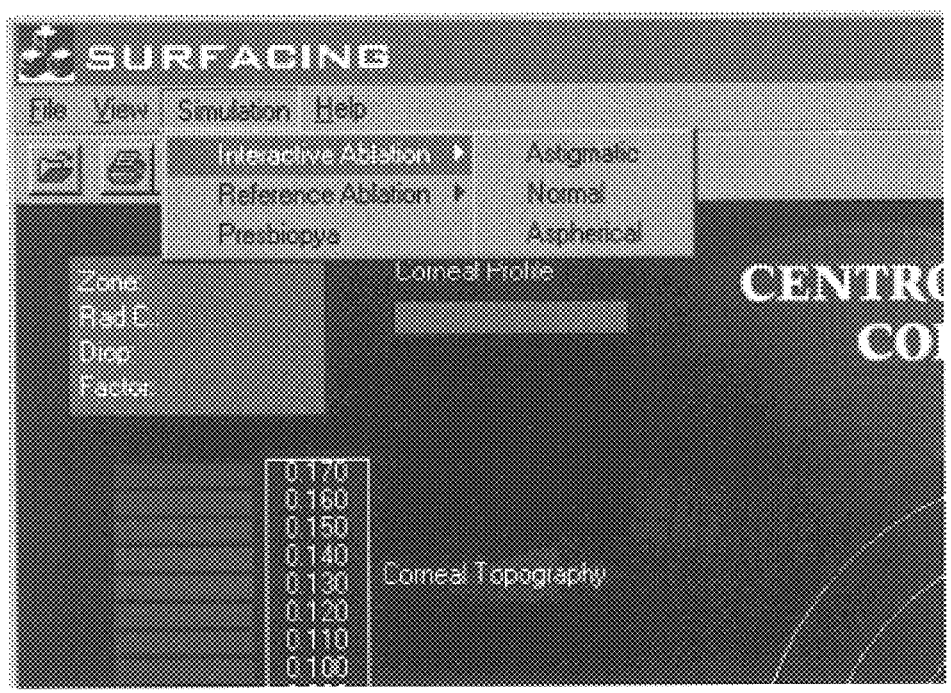
Figure 31:
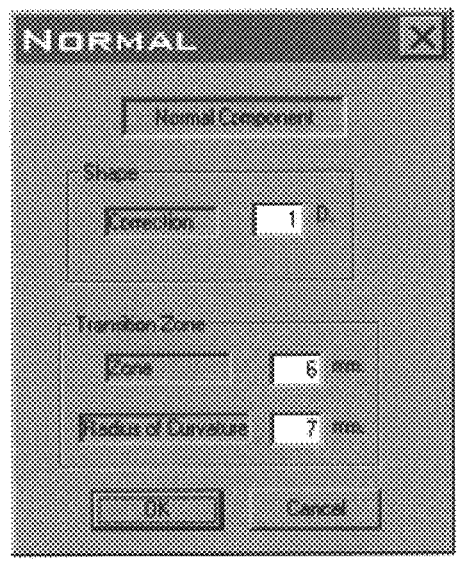
Figure 34:
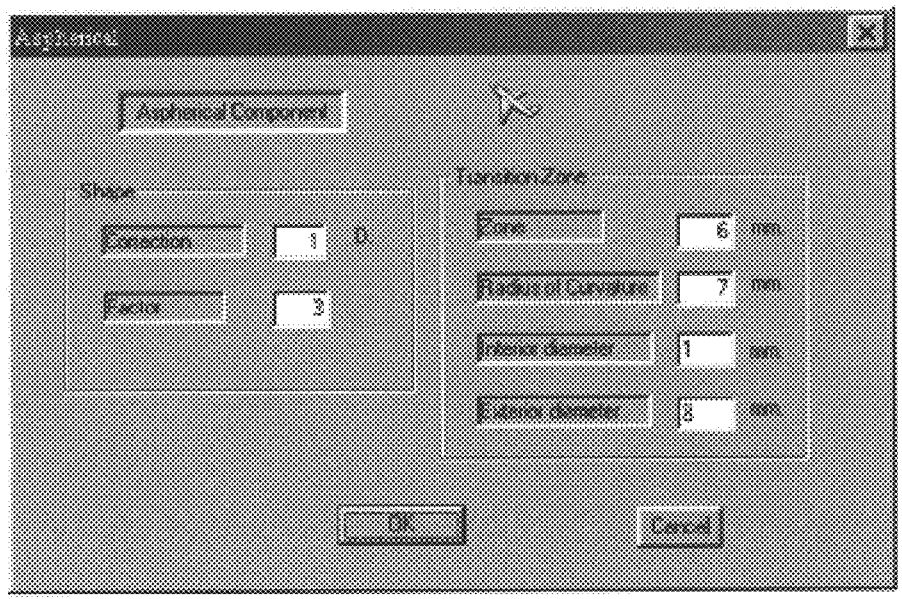
Figure 32:
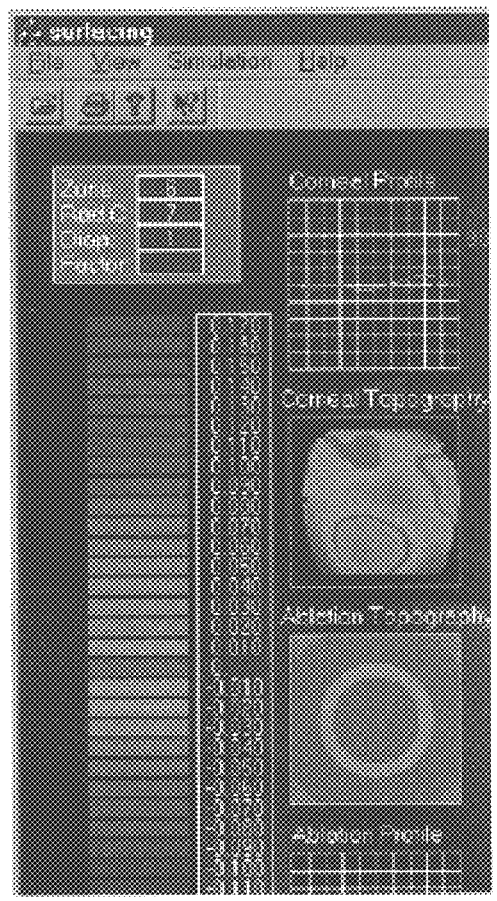
Figure 33:
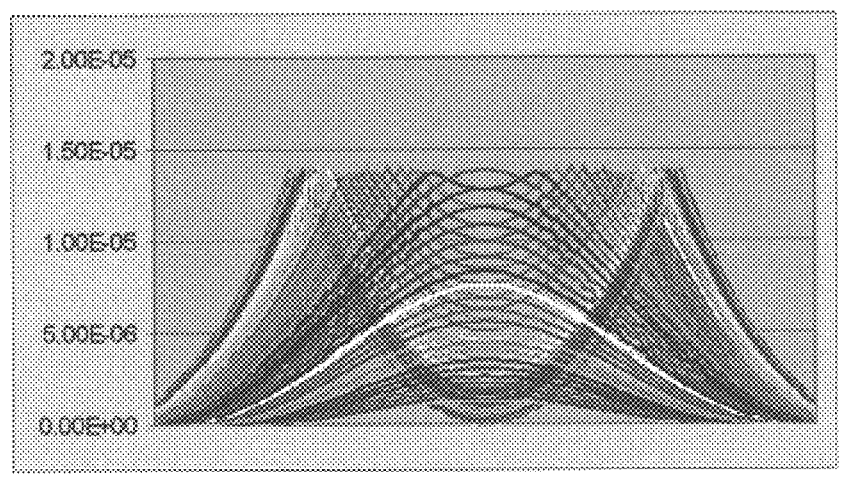
Figure 35:
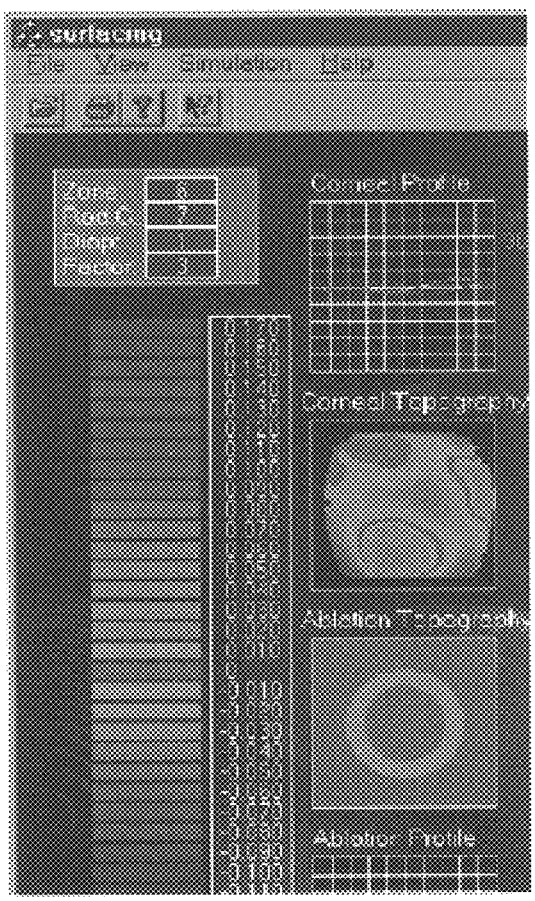
Figure 36:
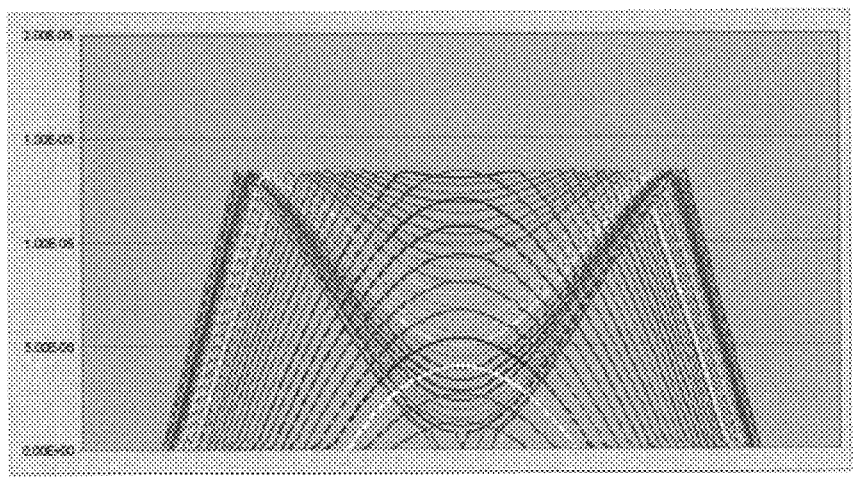
Figure 37:
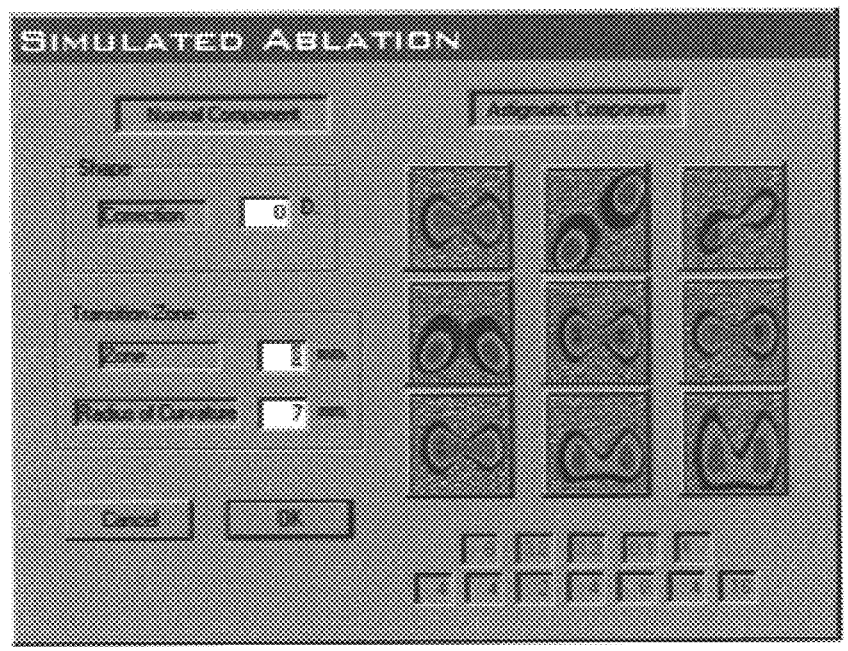
Figure 40:
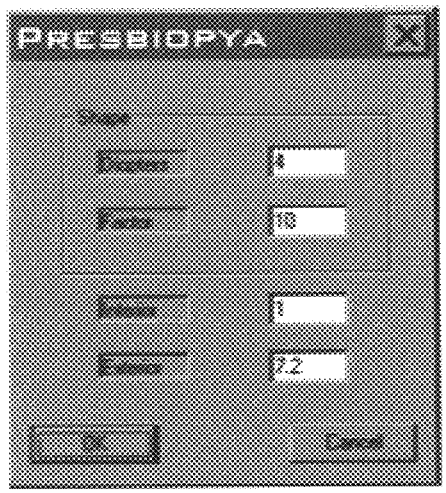
Figure 38:
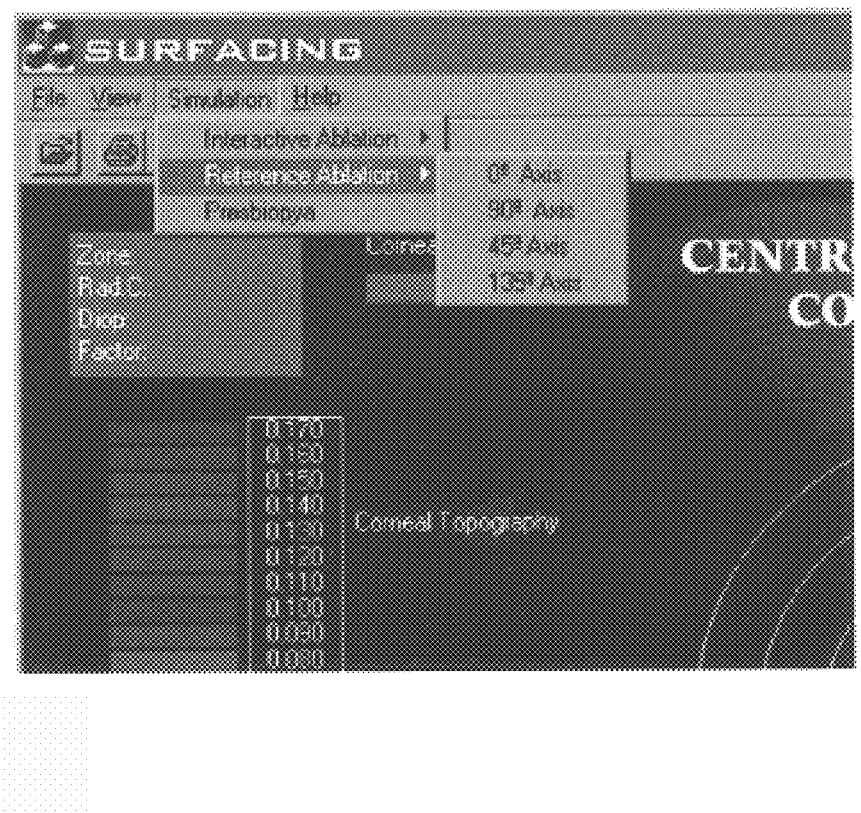
Figure 39:
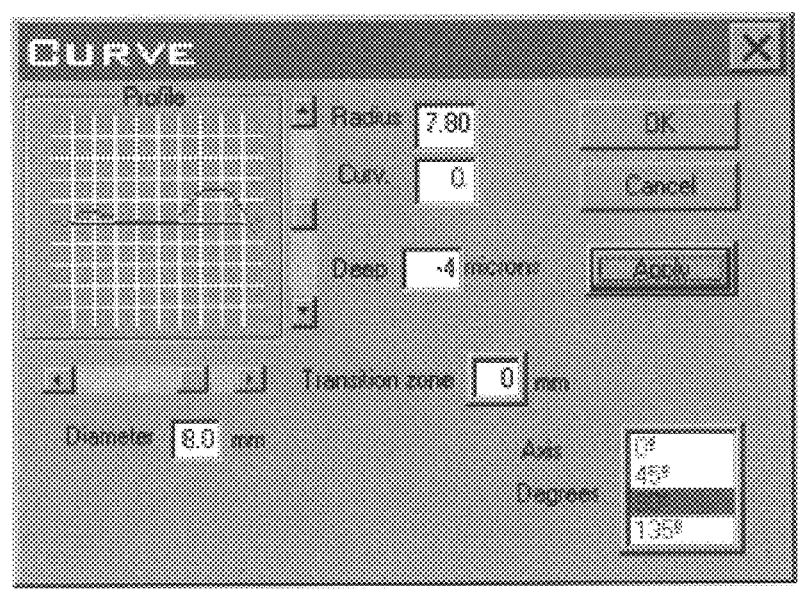

FIG. 29 shows an overlying sub-window illustrating various individual files of topographical data;

FIG. 30 illustrates a pop up screen for choosing a choose procedure option from a plurality of choose procedure options;

FIG. 31 illustrates a normal screen window box;

FIG. 32 illustrates a procedure box for the entering of ablation data during surfacing process;

FIG. 33 provides a line depiction of the normal (spherical) parameters entered in the window box shown in FIG. 32;

FIG. 34 illustrates a dialog window box with a variety of adjustable fields related to an aspherical component of the surfacing procedure;

FIGS. 35 and 36 illustrate views similar to FIGS. 33 and 34, respectively, but under an "aspherical" procedure setting;

FIG. 37 shows an "astigmatic" dialog window box together with data entry regions for ablation data entry;

FIG. 38 illustrates the enter ablation data step involving picking the desired reference axis from the pop up options illustrated;

FIG. 39 illustrates a line contour profile with respect to the reference axis shown in FIG. 38; and FIG. 40 shows a presbyopia dialog window screen with "enter ablation data" locations.

Figure 41:
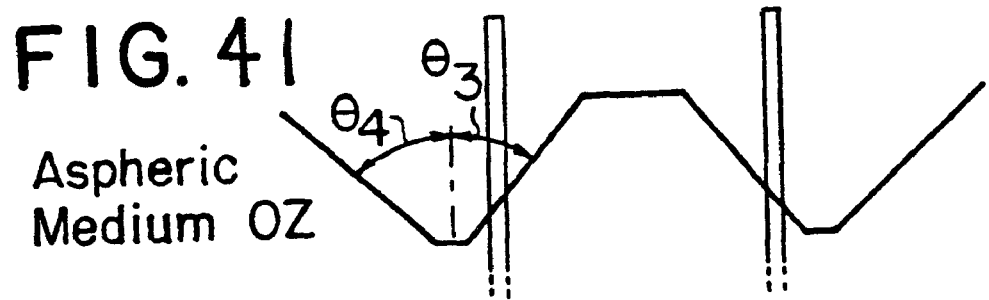

FIG. 41 shows a schematic example of an aspheric presbyopia ablation.

DETAILED DESCRIPTION OF THE PREFERRED EMBODIMENTS

FIG. 1 shows a block schematic view of the flow of data in the system of the present invention from the patient to the laser system. As shown in FIG. 1, the patient's unique eye topography is scanned and mapped by a suitable corneal topographer. The topographer that is used preferably provides sufficient data points to provide a good source for the subsequent data manipulation carried out by the interface system described below. In a preferred system of the invention an elevational topography system such as the "ORB-SCAN II" system manufactured by Orbscan Inc. of Salt Lake City, Utah, US which provides a digitized topography map based on elevation points taken at steps of 10 microns along both the X and Y axis with an elevation resolution generally ranging from 1–5 micron. The ORBSCAN II system relies on data extracted from both a slit lamp and Placido disk acquisition methods. Other topographers may also be used such as topographers using only one of the two Placido disk and slit lamp techniques, although the higher definition combination is preferred from the standpoint of providing a good source of data for downstream manipulation of the interface system of the present invention.

FIG. 2 shows a block schematic view of the system 40 of the present invention which includes topography system 42, interface system 44 and laser system 46. Interface system 44 comprises a visualization system 48 in communication with data processor 50 which carries out the functions described in greater detail below. Preferably interface system 44 further comprises input socket 52 and output socket 54 which are provided to make data conformance functions (if required) in the extracting of data from the topographer and the outputting of data to run laser system 46. Amongst the various functions performed by the interface system, the interface system stores the data in a desired form such as a matrix. This matrix can be stored for different uses including the basis for converting the data into a color map wherein different elevations are assigned different colors to illustrate the stored matrix in visualization system 48. Following the manipulation and customizing of the system by the surgeon until the desired ablation profile is achieved (as described in greater detail below), that final ablation profile is illustrated and placed in a suitable format such as a matrix and output by way of the output socket to the laser system being utilized. The output socket provides any conversions required to make the final ablation data format compatible with the drive parameters of laser system 46.

Laser system 46 includes control means such as a dual X-Y scanning mirror and associated control software and hardware for varying the eye contact position of the laser beam which is used in association with a laser generation means such as an excimer laser, although other suitable corneal stroma removal techniques may also be relied upon (e.g., a fluid jet or mechanical material removing device). The control means of the laser system 46 and the laser beam location means of the laser system are designed to receive customized, fine detailed ablation profiles and carry out the instruction outputted by the interface system such as the aforementioned X-Y-Z final ablation profile matrix. Preferably the excimer laser features a ceramic head able to operate at repetition rates of 200 HZ or higher with a reliable and controllable power output, an adjustable beam spot adjustable from 1 mm to 2 mm. In a preferred embodiment, the laser system is a dual scanner mirror device which moves the excimer beam on an X and Y axis and works in conjunction with an eye tracker system with a scan rate of 2000 to 4000 HZ or higher and a centration device to keep the laser beam steady at the target center (e.g., the pupil center) before surgery to assure that at the beginning of surgery the laser is properly targeted and properly registered with respect to the ablation profile.

A laser system such as the Lasersight 2000 or Lasersight LSX I of Lasersight Inc. (Orlando, Fla., US) provides a laser system that is capable of providing the laser positioning in conformance with the ablation profile directions output by the interface system of the present invention. As a further example of a preexisting laser system which could be used, albeit at a lower speed than preferred, is the Cliron-Technolas Keracor 17 and 217 laser systems of Cliron-Technolas GmbH.

Figure 3:
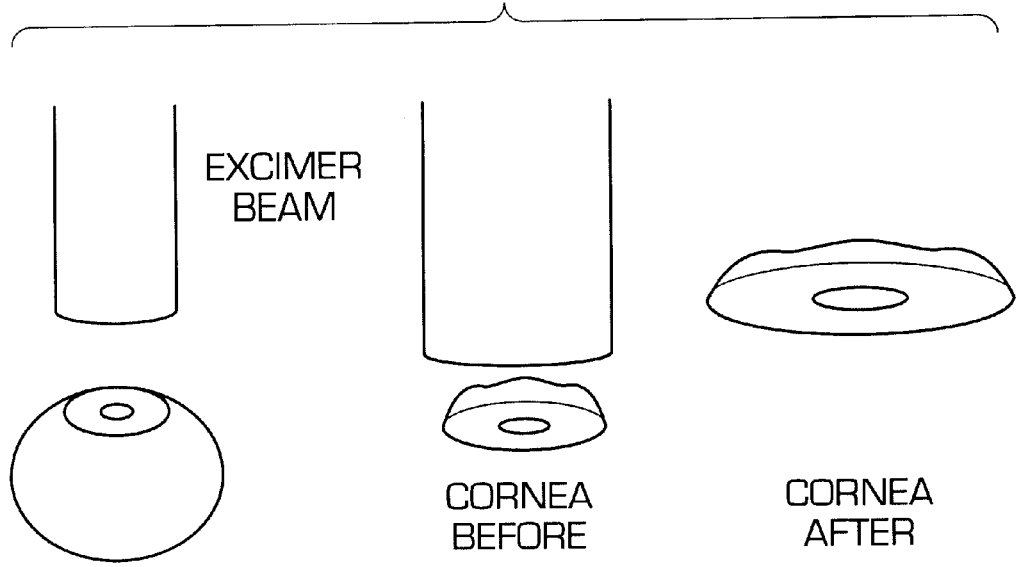
FIG. 3 shows a schematic representation of the retention of surface irregularities and limited ablation profile application involved with prior art systems.
Figure 4:
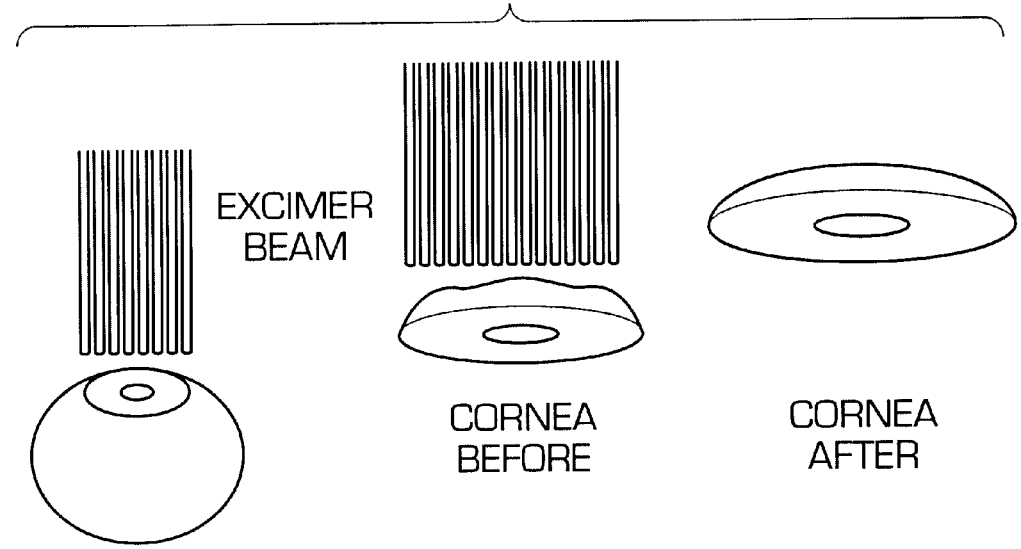
FIG. 4 shows a schematic representation of the removal of surface irregularities and the non-limiting nature of the ablation profile application of the present invention.

FIGS. 3 and 4 provide a comparison between the non-customized and non-fine detail ablation technique of the prior art and one component of the customized, fine detail arrangement ability of the present invention. In FIG. 3 there is shown an eye being subjected to a laser (e.g., a PRK or LASIK process) wherein a single diameter beam is applied against the eye based on a corrective optical formula such as a myopic correction without any consideration to the uniqueness of each individual's eye in regard to topography contour. The same can be said to other prior art ablation techniques such as a flying spot technique that follows one of the optical formula paths (e.g., a circular path or eliptical path). FIG. 3 shows that because the eye has a non-smooth topography, the resultant eye has the same topographical irregularities in the post operative state as it did in the pre-operative state. For example, in a PRK procedure since the beam applied is designed to have a generally constant energy level across its diameter it will ablate away a constant thickness across the treated corneal surface and thus portions of the eye having peaks in the preoperative mode will have those. same peaks in the preoperative mode with the same generally being true with respect to topography depressions. The same can be said to be true with respect to LASIK treatment because the microkeratome presses down on the cornea during flap production and thus any peaks will reappear at the exposed stroma level following the removal of the pressure and single thickness layer of the flap. FIG. 4 shows in schematic fashion the application of the laser in conformance with the actual topography of the treated corneal surface (stroma or further external layer) through use of thousands of small minibeams applied in a pattern and depth to negate or remove topographical irregularities in the eye so as to produce the smoothly contoured corneal topography shown to the right in FIG. 4.

Figure 5B:
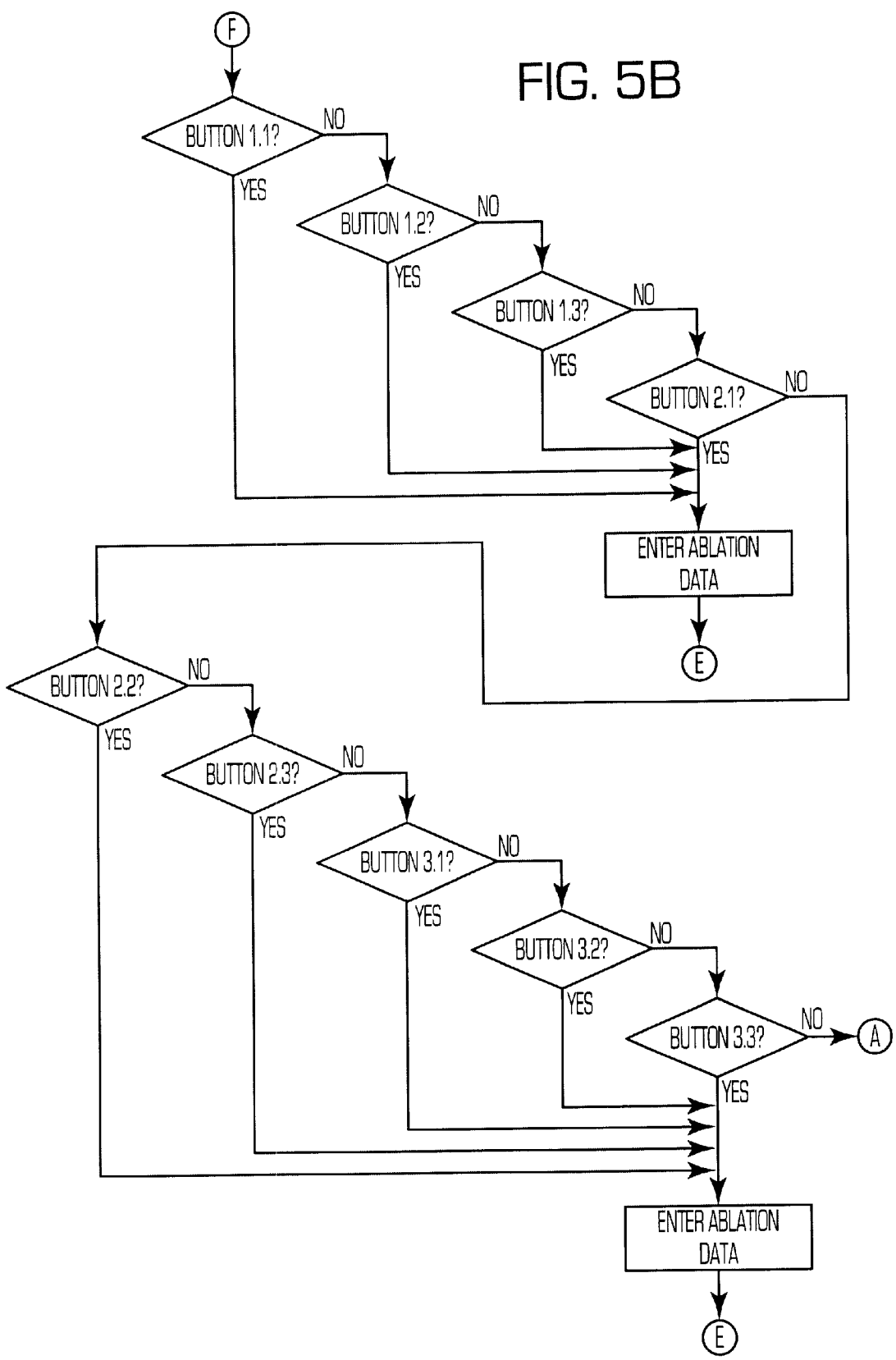
Figure 5C:
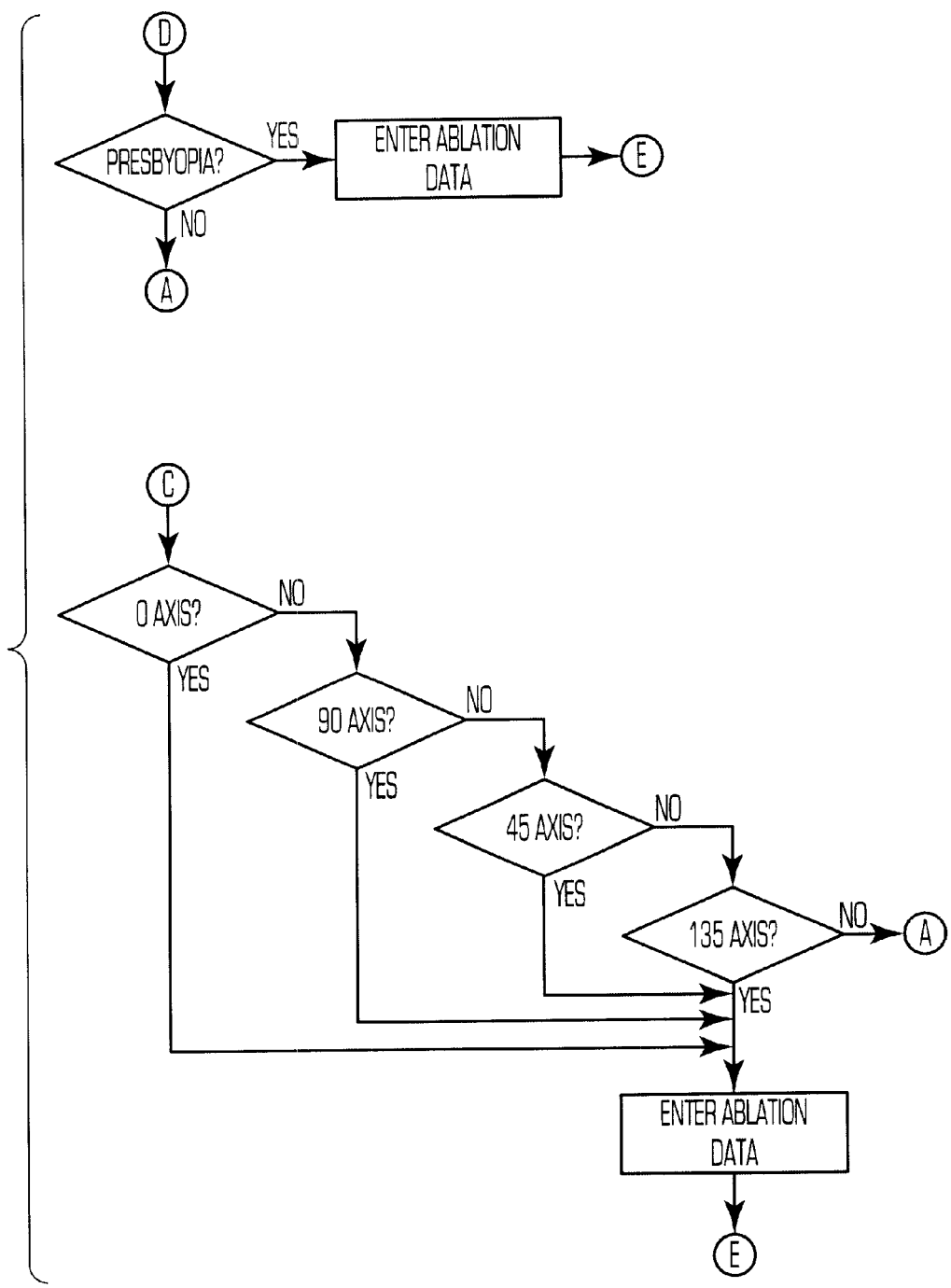
Figure 6:
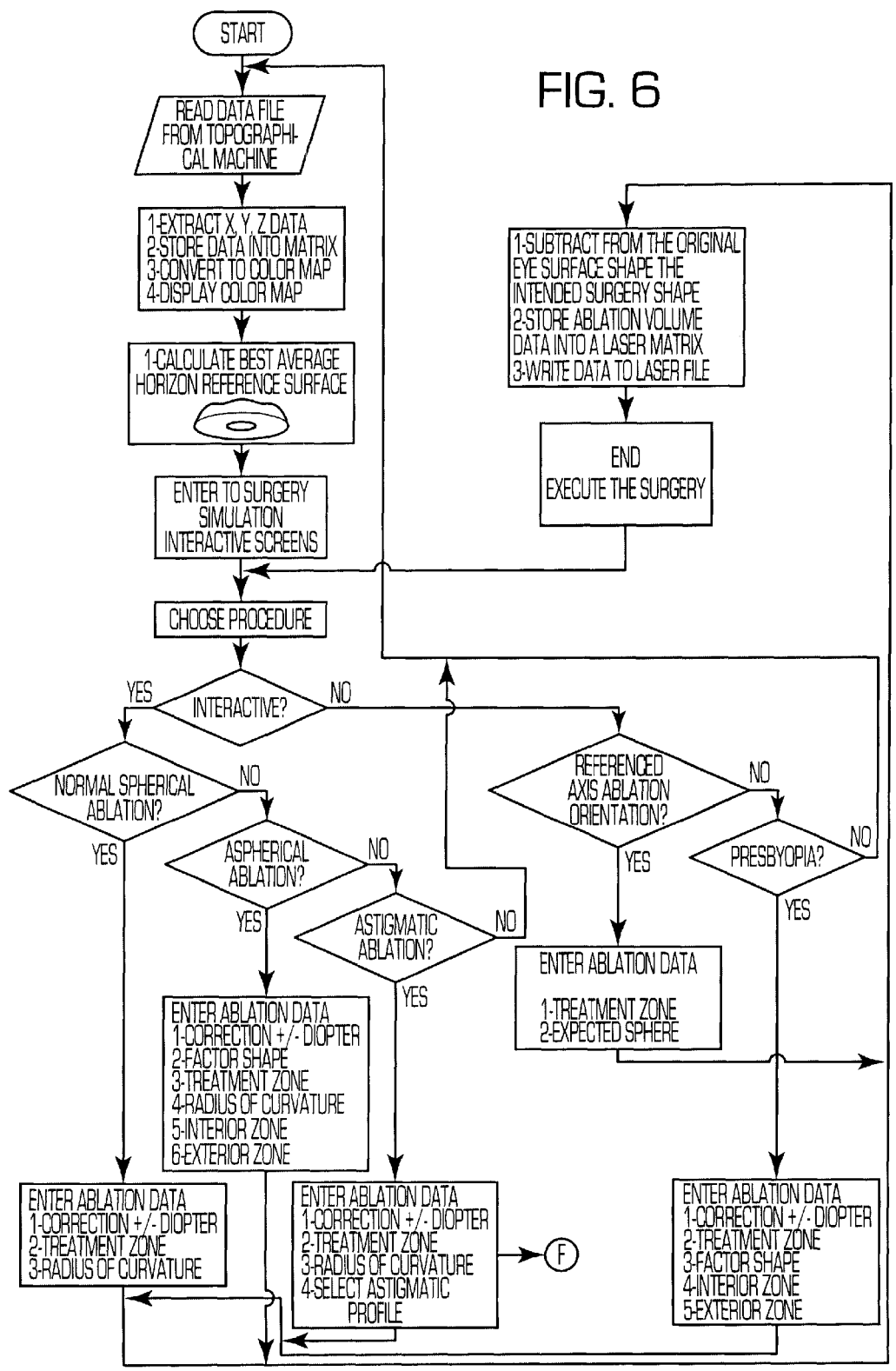
FIG. 6 shows a compacted view of the flow chart of FIGS. 5A,5B and 5C with some added description of possible options and routines carried out.

FIGS. 5A, 5B, 5C and 6 show flow charts depicting the various processing modules and some of the possible routes therebetween provided in a preferred embodiment of the interface system of the present invention. As shown in FIG. 5A, at the start, data output by the topographer is read by interface system 44. As seen by FIG. 6 the formation of the best fit sphere (e.g. Ha median sphere with respect to the actual topography of the eye) is preferably carried out as an initial step immediately following the formation of a matrix based on the data extracted from the topographer. The best fit sphere is a preferred reference location for use as a starting point but as explained below is invariably not the best clinical sphere for patients. The best fit sphere is a mathematical method of interpolating a surface within an irregular surface such as the irregular topography of an eye. Various mathematical techniques can be used such as a spline curve technique or the Bezier technique.

Provided below is a description of a preferred visualization system output of the interface system with reference to FIGS. 28–40.

FIG. 28 shows the opening of the main window of the surfacing file. An additional step includes reading data from a topographical machine which can be stored in individual files as shown in the overlying sub-window in FIG. 29.

The reading data from a topographical machine provides a read structure resulting in a data matrix of 100 per 100 dots acquired over a square area of 10 mm per 10 mm in the eye surface. This means at a step of every 100 microns one dot is read. The procedure permits the operator to choose different eye patient file records to enable the surgeon to execute different procedures or volatile simulations that will generate a control data file in order to operate on the laser machine. A choose procedure step, from a plurality of choose procedure options, can then be carried out. FIG. 30 illustrates a choose procedure step.

The choose procedures correspond to the Simulation option in the surfacing menu bar and permit one to choose three different options: Interactive Ablation, Reference Ablation and Presbvopia.

Interactive Ablation also has three options: Normal, Aspherical and Astigmatic. These options guide the surgeon to three basic procedures.

Normal is a procedure that permits one to make or to simulate ablations with spherical parameters called normal. This kind of procedure corrects myopia and hyperopia.

An illustration of Normal Screen Window box is shown in FIG. 31. In the surfacing process, there is also provided for the entering of ablation data as represented by the procedure box shown in FIG. 32. FIG. 33 provides a line depiction of the normal (spherical) parameters entered in the window box shown in FIG. 32.

This last procedure box is a feature dialog window that contains several parameters oriented to define profile and depth of the ablation.

Correction is the first field. This field accepts negative and positive numbers with negative numbers defining myopic patterns, and with positive numbers defining hyperopic patterns. This field is measured in Diopters.

Zone Diameter is the next field and defines the ablation scope and function like boundary.

Radius of Curvature is the last field and permits one to choose different curvature profiles with the same Diopter value depending on the specific eye curvature.

Aspherical is an option that permits live interaction with this parameter to produce myopic and hyperopic corrections but with aspherical profiles.

FIG. 34 illustrates a dialog window box with the following fields:

Correction expressed in Diopters, it can contain a negative number for myopia and a positive number for hyperopia.

Factor is a convenient parameter that permits one to modify the equation shape in order to reach the desired profile.

Zone Diameter is the next field and defines the ablation scope and function like boundary.

Radius of Curvature is the last field and permits one to choose different curvature profiles with the same Diopter value depending on the specific eye curvature.

Interior Diameter is a parameter that applies only in hyperopic treatments and indicates the interior zone that should not be touched.

FIGS. 35 and 36 illustrate views similar to FIGS. 33 and 34 but under an "Aspherical" procedure setting.

Exterior Diameter in the same way like the previous field only applies on hyperopic treatments and permits one to truncate the exterior effect due to curve profile.

Astigmatic is the last option and is related with a dialog window that contains graphic buttons which provide visual relationship depiction as between different curve profile representations.

FIG. 37 shows an Astigmatic dialog window box together with the below described data entry regions for ablation data entry.

Correction expressed in Diopters, define the quantity of approximate tissue to be removed.

Zone defines the ablation scope and function like boundary.

Radius of Curvature is the last field and permits one to choose different curvature profiles with the same Diopter value depending on the specific eye curvature.

In addition FIG. 37 illustrates fields that correspond to coefficients that depend on the selected button and operate like profile modifiers.

Reference is an option that basically permits one to observe the corneal profile along different axis. These main axis are 0,90,45,135 degrees. Once the steepest or flattest axis is selected, the surgeon can execute different procedures to reach the best performance in accordance with his experience.

FIG. 38 illustrates the enter ablation data step involving picking the desired reference axis from the pop up options illustrated while FIG. 39 shows the contour profile with respect to the reference axis chosen in FIG. 38.

With the Apply option one can magnify the cornea profile in the indicated axis and show an interactive graphic that permits the operator to slide a line over the cornea profile and simulate a blade that theoretically should remove so much tissue like appears in the graphic.

Furthermore, this mode offers additional interactive parameters in order to modify the diameter of the ablation zone, transition zone and show average curvature and radius for this specific profile.

Presbyopia is the last option that has a dialog window with four parameter that permits an operator to modify lightly the profile ablation.

FIG. 40 shows a presbyopia dialog window screen with enter ablation data locations.

Diopters basically represents the ablation depth.

Factor is a convenient parameter that permits an operator to modify the equation shape in order to reach the desired profile.

Interior Diameter is a parameter that indicates the interior zone that should not be touched.

Exterior Diameter permits an operator to truncate the exterior effect due to curve profile.

As particularly shown in FIGS. 3,5A–C, 6 and 7, the surgeon has the option of choosing the reference module of the present invention's interface system. The reference module, which involves the determination and application of a best clinical sphere, is particularly well suited for highly irregular eye configurations that involve astigmatic or myopic correction, but is also well suited for more typical astigmatic and myopic eye corrections and has shown to provide a more predictable result as compared, for example, to a formula based astigmatic correction.

Figure 6A:
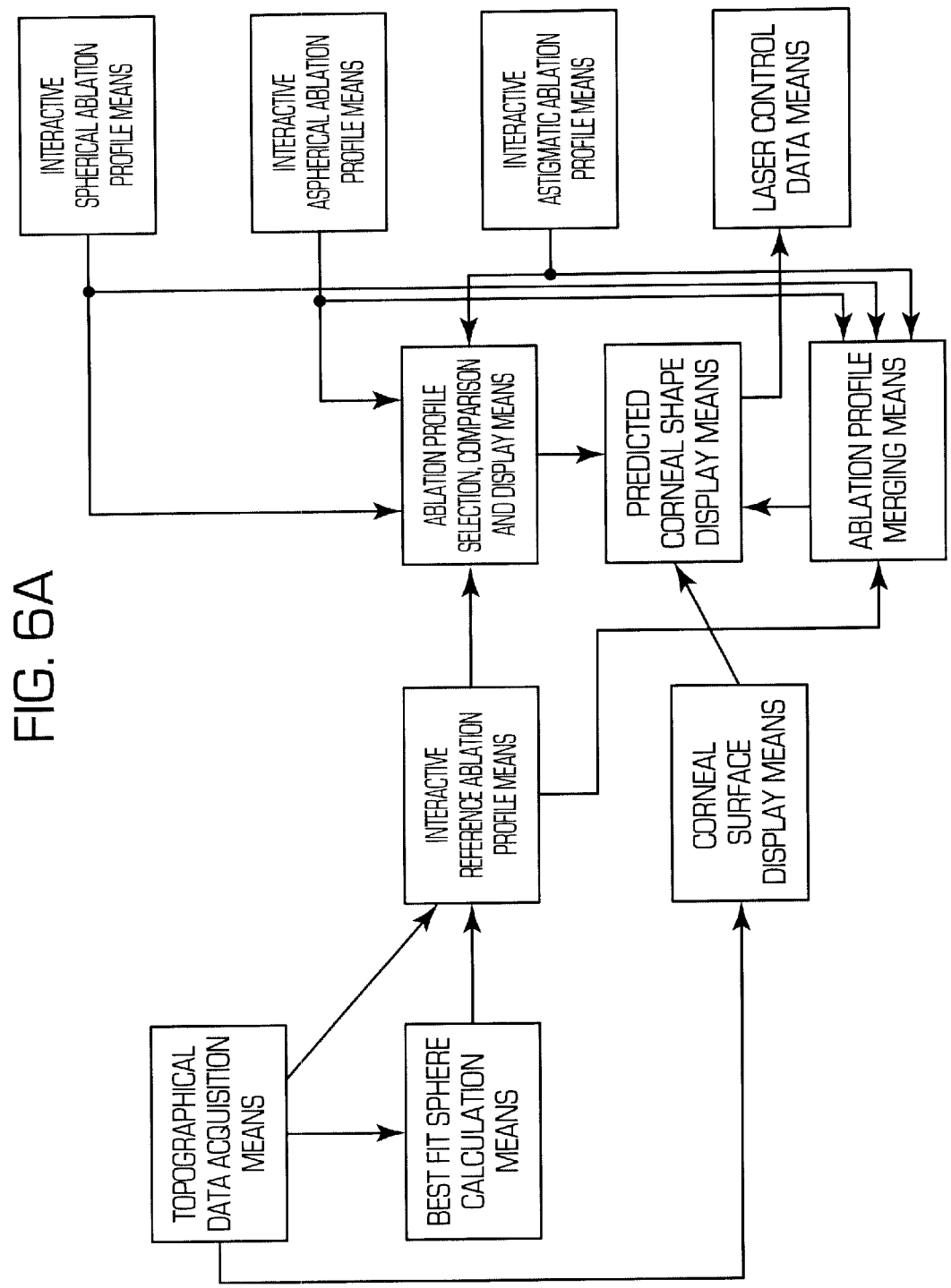
FIG. 6A is an embodiment of an ablation control apparatus.
Figure 7:
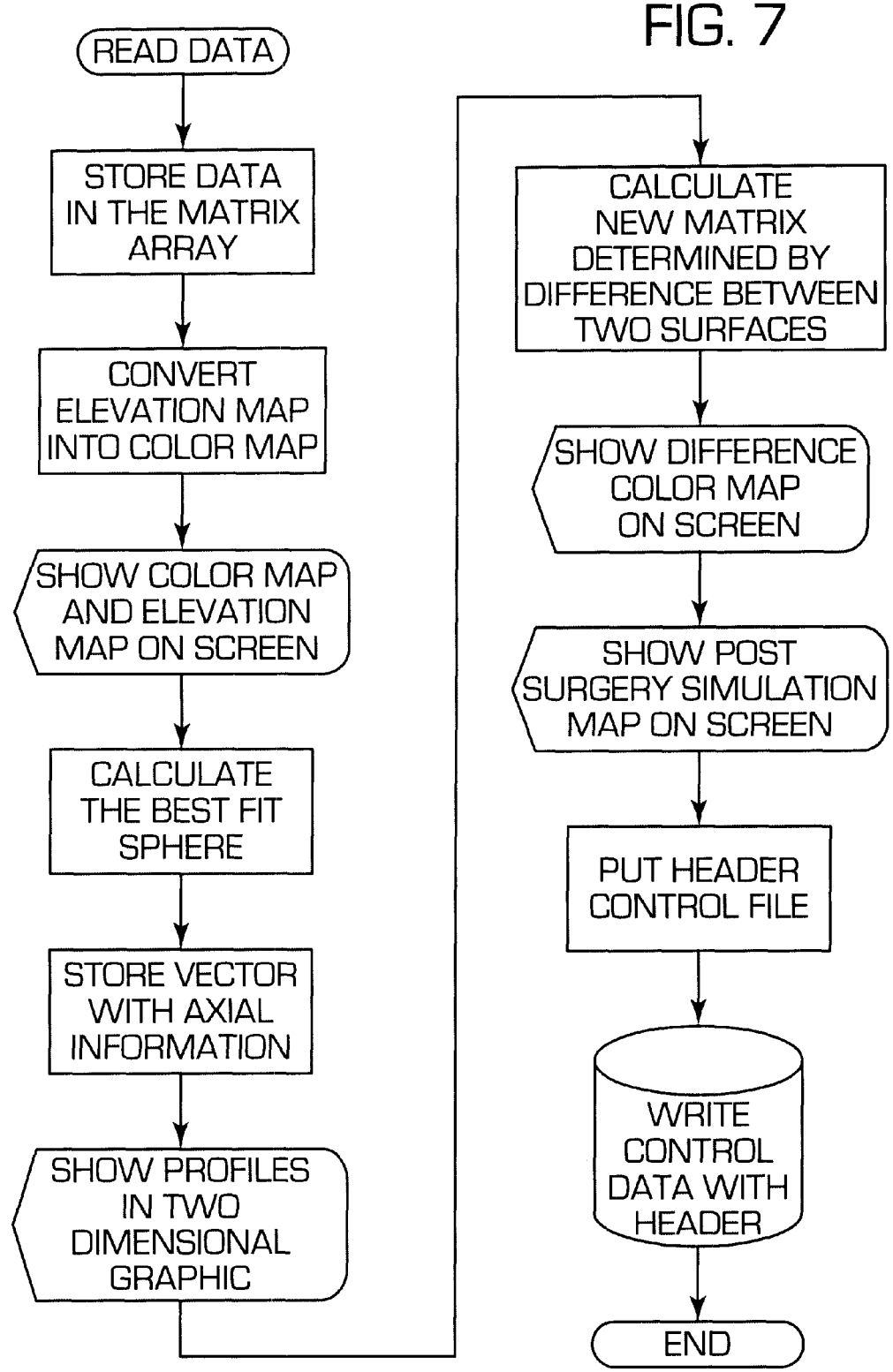
FIG. 7 shows a flow chart of the process involved leading to and while within a reference module of the interface system of the present invention.

A typical block diagram of the laser ablation control apparatus is given in FIG. 6A. It should be understood that the various means illustrated with blocks in the Figures are preferably implemented using software, and thus these means can be embodied by a single microprocessor programmed with the software for implementing the means. However, those of ordinary skill in the art will also understand that each of the means illustrated with blocks in the Figure can alternately be embodied by a specifically wired circuit.

The apparatus shown in FIG. 6A includes a topographical data acquisition means which receives the corneal surface elevation map from the topographer. The corneal topographical data which is acquired can be displayed by the corneal surface display means. Preferably, this surface is displayed as a color encoded surface elevation map. A best fit sphere calculation means generates a spherical fit of the data acquired by the topographical data acquisition means. The spherical fit is performed along a chosen axis by the user or is fit based on a pre-configured default axis. Based on the acquired topographical data and the selected best fit sphere, a reference ablation profile is generated and can be interactively modified to produce a surgically acceptable reference ablation profile. Other ablation profiles can be selected and individualized by the user to optimize the profile for the individual cornea. The apparatus has means for generating these profiles in an interactive fashion. An interactive spherical ablation profile means, interactive aspherical ablation profile means and interactive astigmatic ablation profile means are included in the preferred embodiment.

An ablation profile selection, comparison and display means allows the user to select the type of ablation profile to be displayed and considered for the ablation procedure. One, two or more ablation profiles can also be displayed so the user will have a visual comparison of the profiles. A predicted corneal shape display means prepares and displays the predicted corneal surface elevation maps that will occur if the selected ablation profile(s) are applied to the patient's cornea. The prediction is calculated by a subtraction of the ablation profile from the corneal topographical data and can include corrections based on physiological models of corneal mechanical properties and corneal healing properties. If the predicted corneal shape is satisfactory, the ablation profile is written to the laser control data means to allow the corneal ablation to be executed. In some situations, it is preferable to merge a reference ablation profile with one of the other ablation profiles. An example of such a situation would be when a correction for astigmatism is performed by a reference ablation and results in a myopic cornea. In such a situation, a hyperopic ablation profile may be merged with the reference ablation profile data to produce a merged ablation profile that will correct the astigmatism in a manner that does not induce myopia. The result of the execution of the merged ablation profile can be predicted by comparison to the corneal surface elevation map by the predicted corneal shape means. As before, if the predicted corneal shape is satisfactory, the ablation profile is established and then written to the laser control data means to allow the corneal ablation to be executed.

FIG. 8 shows a preferred, main visual screen for the reference module which depicts an irregular eye topography having emphasis along the 90° axis with an overlying sub window showing a cross section of the cornea profile along that same axis as well as a proposed best clinical sphere location reference ablation line having been moved to a location that results in a diameter of 8.6 mm and a depth of 24 microns with reference to the original fit reference sphere. The best clinical ablation reference line is shown to be essentially at the lower most point of the topographical profile along the 90 degree axis. This same overlying sub window appears in the lower left hand corner of FIG. 11 with FIG. 11 further providing additional overlying sub windows showing the same proposed best clinical sphere elevation but along each of the axes options made available under the reference module of the present invention. FIG. 10 shows on the other hand a plurality of different elevations for proposed best clinical spheres. In FIG. 10 the upper left corner overlying window shows a proposed best fit clinical sphere reference line that has been shifted up with respect to the originally determined best fit reference sphere found in the lower left hand window of FIG. 10. The "deep" designation appearing in each overlying sub window represents the elevation difference between the shifted proposed best clinical sphere reference line and the original best fit sphere reference line. Thus in the lower left hand sub window "deep" is shown as 0 which is indicative of the proposed best clinical sphere being on the same level as the original best fit sphere. The positive value 76 for deep in the upper left corner sub window is indicative of the proposed best clinical sphere reference line being placed above the original reference line. Together with the deep value, the pop up sub windows in FIG. 10 each show the radius and curvature (in diopters) of the proposed best clinical sphere. The elevation change in the reference line is made easy through use of the sliding scale to the right of the profile grid in each sub window. In addition, there is a horizontal sliding scale which allows a surgeon to control the diameter of the proposed best clinical sphere ablation profile.

FIG. 8A illustrates a two dimensional profile along a single axis of the cornea's topography (e.g., representation of an exposed corneal stroma topography) 100, the two dimensional depiction of the fit reference sphere 102 and the two dimensional depiction of a shifted proposed best clinical sphere. In addition, FIG. 8A shows at 106 the additional removal of tissue that might be required in a combination situation wherein an added compensating hyperopic ring ablation is deemed desirable to compensate for any inherent corrective changes that show up in a simulation of the best clinical sphere ablation chosen in the reference module. At the bottom of the main topography view of the eye's surface, there is indicated "Diff". This value is equal to the elevation difference at any point on the X-Y plane between the actual topography minus the fit reference sphere elevation value plus the difference between the fit reference value minus the chosen best clinical sphere elevation (i.e., Diff= (topography—fit reference sphere)+(fit reference sphere—best clinical surgical sphere)). This value can be chosen along any location on the topographical location on the central main topography map by moving a pointer to the desired location and clicking. The diameter (based on two times the radius of the pointer out from the pupil center) and the diopter value for the designated point is also displayed below the main topographical map. FIG. 18A shows an example of moving a pointer onto a particular location of the main map.

FIG. 8A also shows the earlier noted "deep" value 110 which represents the difference between the fit reference sphere elevation and the best clinical sphere elevation with respect to a particular point along a common axis. FIG. 8A also shows a combination situation involving an added ablation (e.g., a hyperopic equation profile) combined with the best clinical sphere ablation chosen in the reference section of the interface system. A discussion of combination ablation profiles is provided in greater detail below.The final ablation profile coordinates or data that is to be fed to a laser system can be determined based on the known parameters of the added equation based hyperopic ablation ring (e.g. another matrix based on a 360 degree rotation of a chosen two dimensional hyperopic ablation cross-section). Since the topography matrix (or other means for fixing coordinates in a workable medium), fit reference sphere matrix, best clinical sphere matrix, and elevation matrix for the rotated hyperopic profile are known, the full ablation profile (representing the tissue to be removed) matrix (one elevation value represented by 115) can be determined through use of these determined parameters. For instance, an ablation volume determination by the known distance 112 between the topography matrix and the best clinical sphere matrix 112 plus the added depth 113 or the combination of the known elevation difference between the topography and fit reference sphere 116 plus the elevation difference between the fit reference sphere and best clinical sphere 110 plus distance 113. Various other values can also be displayed and/or utilized such as the distance between the added hyperopic ring ablation and the fit reference sphere 114.

A surgeon makes an initial determination as to what is considered to be the best of the various proposed best clinical sphere elevations for the common 90 degree axis profile shown in each sub window in FIG. 10. If a decision is made that the lower elevation or depth value of −24 depth seems to best suit the situation the surgeon can then proceed to considering how the initially chosen best clinical sphere performs along the other axes options of 0,45, and 135 degrees. As noted above, FIG. 11 shows the initially deemed best clinical sphere taken along each of the four axes options. In this way the surgeon can consider whether the initially deemed best clinical sphere remains considered the best when its relative positioning to the actual topography of the eye is analyzed under the different axes settings. After determining that no adverse effect would result with the initially deemed best clinical sphere, the surgeon can then activate the "apply" function key to see what the simulated post operative eye would look line with all tissue removed above the best clinical sphere which is to provide an ablation profile designed to produce a desired post operative curvature radius of 8.03 mm and a refraction of 39.5 diopters.

FIG. 9 illustrates the results of the apply function activation based on the above described determination of the best clinical sphere profile to apply. FIG. 9 again shows in the larger topographical view the actual eye topography matrix while to the left of that view there is shown the corneal profile along two axes (0 and 90 degrees in this case) and the simulated resultant corneal topography in the upper two depictions and the ablation topography and ablation profile to be implemented to remove the tissue required to remove all tissue between the surface of the eye represented in the larger topographical illustration to the best clinical reference sphere chosen. The simulated outcome shows a generally consistent color near the green or neutral "0".

FIG. 12 illustrates another example of where the surgeon is able to use the present invention to conform the ablation profile to be applied to best suit the individual's needs which in this case involves a combined reference and normal ablation profile which combination is made by the interface system such that a single ablation profile is formed for use in directing the laser system (e.g., the system determines the best single ablation profile to be implemented in a single laser run based on the matrix value associated with the applied best clinical sphere and the required even lower elevation values associated with the ablation depth and configuration of the normal equation correction deemed required). The particular combination simulation in FIG. 12 depicts a surgical procedure for astigmatism and a regular hyperopic profile that is needed because the highly irregular central astigmatism correction will induce hyperopia due to the flattening of the cornea during the reference ablation to an extent not needed for this patient. That is, the reference ablation inherently generates is this situation a myopic correction which induces a degree of unwanted hyperopia, and this unwanted hyperopia can be compensated for by ablating a hyperopic correction (an annular ablation ring), that acts to steepen the cornea back again to its original shape. The right side showing in FIG. 12 shows the simulated reference ablation results and the left side shows the combination of the two proposed surgeries. In the same way that a surgeon could combine myopia and hyperopia with a referenced ablation, a surgeon could do the same under the present invention can do the same with astigmatism with formula.

FIG. 13 shows a combination of a referenced ablation with a regular myopic pattern based on the fact that on the 90 degree axis the correction induces myopia. In other words, in removing the tissue falling above the chosen best clinical sphere a partial hyperopic correction ring is inherently formed as part of the ablation process over a portion of the cornea. Thus, a myopic correction pattern is provided to compensate. The right side of FIG. 14 shows the referenced ablation and on the left side the result of the combined treatment is shown. The central button removed by the myopic correction pattern can be seen by the central depression illustrated by the ablation profile taken along the 0 degree axis in the upper left view under the heading "corneal profile" while the corresponding ablation profile to achieve that removed central button of tissue is best shown by the ablation profile along the same axis which appears in the lower left corner view.

As illustrated by the flow chart in FIG. 5A the surgeon may determine that the eye correction involved does not suggest the use of the reference module either alone or in combination with one of the interactive module's sub modules designated normal, aspherical, astigmatic, but instead suggests the use of the interactive sub modules alone. For example, under conditions where the presurgery corneal topography is substantially regular, it is possible to correct the optical defects of hyperopia and myopia using an ablation profile based on a spherical or aspherical equation. In the case of an astigmatic cornea, an ablation profile may be generated by a member of a specialized library of functions specifically created and optimized for correction of astigmatism. These would be situations deemed by the surgeon not to fall within the category of an irregular corneal topography condition wherein a reference ablation profile may be generated to correct for the topographical irregularities and merged with a spherical, aspherical or astigmatic profile to correct the general corneal defect such as hyperopia, myopia and astigmatism. The combination of a reference and astigmatic formula correction is unlikely however as the reference module is sufficient to handle most astigmatic correction requirements as explained in further detail below. As noted above, the result of such a combination merger is a single ablation profile used to control the ablation laser. Frequently, the use of such a merged profile can result in a successful corneal correction with a minimum of stromal tissue removal. A cutaway 3-dimensional view of the spherical hyperoptic ablation profile is shown in FIG. 24. A cutaway 3-dimensional view of the aspherical hyperoptic ablation profile is shown in FIG. 25. The smoother geometry of the aspherical ablation profile over the spherical ablation profile can result in better corneal healing and improved stability of the correction over time.

FIG. 26 shows a comparison of a spherical ablation profile with an aspherical ablation profile for hyperopia correction. Profile I shows a typical spherical ablation profile wherein the shape of the central concave portion of the profile is governed by a given radius of a sphere and the width of the opening of the concavity. The radius and width parameters are independently selectable by the physician to individualize the ablation profile to the specific cornea. Profile 2 shows an aspherical ablation profile wherein the shape is determined by the appropriate function for either hypermetropia or myopia and the shape of the transition zone is governed by the appropriate selection of the parameters of zone size, radius of curvature, interior diameter and exterior diameter which are selected to individualize the ablation profile to the specific cornea. The aspherical function is itself a formula based on a double quadratic component and an arctan function.

Figure 27:
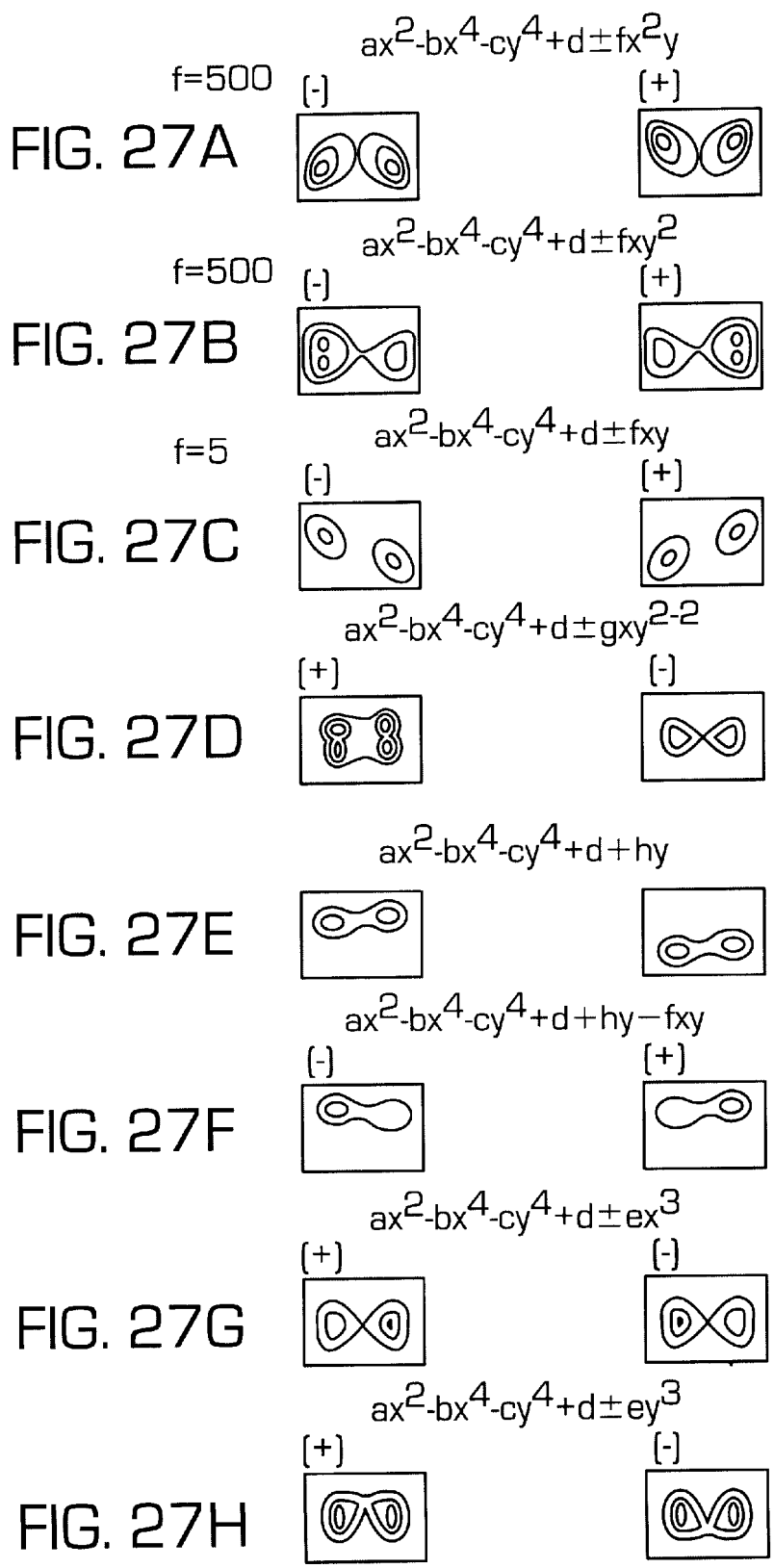

When the cornea is astigmatic but the overall corneal topography is regular, specialized functions may be selected from the library. Examples of the functions in comprising a library for astigmatism correction are shown in FIG. 27. Above each library surface in FIG. 27 is the mathematical expression representing the ablation surface defined by the respective function: The astigmatic correction functions may be individualized for a specific cornea by surgeons adjustment of the coefficients, a, b, c, d, f, h, etc. Note also the earlier description and depiction of an astigmatic reference ablation library under the screen heading "simulated ablation" with means to vary the particular parameters based on manipulation of the surgeon imputed values.

As shown in FIGS. 27A–H, each equation has a common base "$(ax^2 - bx^4 - cy^4 + d)$" plus different equation endings, some of which have common components and vary as to + or −. As shown in FIG. 27H, a double mound topography is one possible result.

The predicted results of the ablation procedure are generated by subtraction of the ablation profile from the corneal topographical map and the resulting predicted corneal surface can be displayed. FIGS. 14 and 15 show screen images of a comparison of spherical ablations and aspherical ablations. The imaged corneal topographic map is shown in the center of each figure. The bottom right image is the selected spherical ablation profile. The top right image is the predicted corneal topography following a laser ablation of the corneal stroma according to the spherical ablation profile. The bottom left image shows the aspherical ablation profile. Above the aspherical ablation profile (top left) is the predicted corneal topography following a laser ablation of the corneal stroma according to the aspherical ablation profile.

FIG. 14 shows a comparison between two myopic treatments of +5 diopters. In some instances an aspherical configuration for the ablation profile is helpful in providing a smoother transition, but since the tissue profile removed in each is different it is helpful for a surgeon to visualize the simulated effect on the eye for each. This comparison screen in FIG. 14 provides such a comparison tool to a surgeon to facilitate the making of the clinical determination for that particular patient's requirements. FIG. 15 provides another example of the benefits of this comparison mode between an aspherical ablation profile in that it shows that an aspherical approach avoids what might be deemed an over ablation ring (lower right corner) which does not occur for an aspherical approach for a common +10 diopter approach.

FIG. 16 shows the imaged corneal topographic map in the center with an ablation profile for a astigmatic correction in the lower left. The top left image is the predicted corneal topography following a laser ablation of the corneal stroma according to the astigmatic function ablation profile. FIG. 16 also shows the ability to compare previous post operative status of a patient and a simulation of what additional treatment will provide for that patient based on a new ablation profile to a previously treated eye or it can be a previous conducted simulation deemed best suited for comparison. Also the results of FIG. 16 illustrate the predicted topography results for a mathematically based ablation treatment can be less predictable than in the reference approach due to the manipulation of many coefficient factors in the mathematical approach under the sub interactive astigmatism module.

FIG. 17 shows an example of a comparison between a reference approach to a particular ablation pattern and the use of the interactive formula based astigmatic sub module. The left side of the view shows the reference approach and the right side shows the formula approach which is also helpful to a surgeon in determining which approach is better suited for the situation (clearly the reference approach produces a better result for this particular patient).

FIGS. 18A and 18B show main view screens of the opposite (right) eye of the same patient shown in FIG. 9 with FIG. 18A being at one proposed best clinical sphere elevation level and FIG. 18B being at a different elevation level. FIG. 19 shows two alternate final ablation profiles to achieve two differently positioned proposed best clinical spheres on the same eye with the left best clinical sphere being set about 20 microns lower than the right one. FIG. 20 shows, for a different patient, similar views as that in FIG. 19 for two proposed best clinical sphere settings at elevations about 20 microns apart. These depictions can be provided on a visual screen to allow the doctor to further review the situation. This can include the ability to rotate the view of the profile to obtain a different perspective of the volume of tissue intended for ablation as shown in FIG. 21 for the ablation profiles in FIG. 20. The matrix associated with the finally determined ablation profile is then sent by the interface system via the output port to the laser system to govern the activity of the laser beam to produce the desired ablation in the eye.

FIGS. 22A and 22B show schematic views of a preferred laser pulse application approach which involves controlling the preferred laser location control means which is preferably an X-Y based scanning control system which is well suited for the preferred elevation mapping along a Z axis with respect to an X-Y plane approach described above. The ablation profile data package (e.g. a file with the final ablation profile determination) provides the required information for governing the travel of the laser beam to ablate only those areas of interest as determined by the final ablation profile. In the preferred embodiment the laser is first directed to apply a series of random pulses over an area or areas of the cornea which corresponds to the base area or areas of the ablation profile. The process is repeated in sequence by applying laser patterns corresponding to areas of tissue falling within an elevational slice of the ablation profile. This ablation technique is schematically shown in FIG. 22A wherein, at the start, a series of pulses are applied (in random fashion across the X-Y axis plane to avoid localized heating) along the single X-Y plane of tissue represented by L1 with the shape governed by the corresponding periphery or peripheries represented by the the ablation profile such as those shown in FIG. 20. After the first area represented by the base plane is completed, the laser repeats a random pattern of pulses along the next ablation profile level (the next stack of pulse units shown by the brick like blocks in FIG. 22A falling at level L2) within the X-Y slice boundary or boundaries for that level. This is repeated until there are no longer any additional elevation slices of tissue left in the ablation profile representation (L1, L2, L3 . . . Ln).

FIGS. 5A–C also include a presbyopia module which is an option that a surgeon can chose in place of the other module options of reference and interactive (although a combination approach of reference/presbyopia formula is also possible such as in the above described combination approaches). Under this module a surgeon can treat for presbyopia by applying a presbyopia correction ablation profile in accordance with the parameters fully set forth in the above noted and incorporated U.S. Pat. No. 5,533,997 and U.S.Ser. No. 09/186,884 filed Nov. 6, 1998. The presbyopia correction can also be made as a separate ablation run following an earlier refractive ablation run such as an astigmatism correction.

FIGS. 23A–D show a plurality of ablation calibration runs governed by ablation profiles determined by the interface means of the present invention with the ablation being close to or at completion. The substrate material shown in the visualization screens (video segments) of FIGS. 23A–D illustrate a substrate which is comprised of a material capable of showing a representation of the depth of tissue a laser would remove following the received ablation profile. In a preferred embodiment photographic paper that has been exposed and thus blackened is subjected to the laser profile and the different color laminates of the photographic paper are revealed or not revealed depending on the degree of laser exposure such that those areas subjected to repeated pulse hits show up as a different color as compared to those areas not subjected to as many hits. Thus the substrate provides a good visualization of the ablation pattern that would be formed in the eye (as compared to the prior art's application to black single color paper showing only the outline of the base layer of the ablation profile). The substrate can be formed so that the color layers shown generally correspond to the colors appearing in a topographical map so as to use similar visual coding. The lower left hand of each view screen in FIGS. 23A–D can also be provided with a predicted or established full ablation cycle time (e.g., 15 seconds for the FIG. 23A illustration) and a larger and centralized time depiction revealing the actual time at which the laser has run to reach the ablation color pattern shown in the figures (e.g., 14 seconds for the FIG. 23A illustration).

In carrying out an ablation of a patient's eye, the laser is driven to remove a volume of tissue from the eye that is dictated by the ablation profile data package. This data package can be transferred directly to a linked laser system or the interface system can be used in a remote fashion. For example topography data files can be transferred on an appropriate medium such as a computer disk and the disk sent to a separate location where the interface system is located. A surgeon at the interface system location can process the topographical data obtained and determine what the best clinical approach would be with the assistance of the interface system. The ablation profile data package can then be transferred to the facility where the surgery is actually to be performed. In this way surgeons with more expertise or experience can provide ablation profile packages. Another possibility made available by the present invention is that it allows one surgeon to prepare an ablation profile with the interface system for transfer to another surgeon having the interface system of the present invention for any suggestions or alterations. In addition, because of the versatile nature of the present invention, a combination topographer/interface system can be located independent of a laser system and a laser system located at a separate location or the topographer can be located at a separate location from the interface system and/or laser system.

FIG. 41 shows an example of an aspheric ablation for presbyopic treatment with a relatively medium ablation zone profile (OZ), with OZ>1.3 mm and an exterior limit<7.8 mm. $\sigma_3$ and $\sigma_4$ represent the angles of the respective sloped side walls shown in FIG. 41.

The present invention is particularly well suited for use in a LASIK procedure that typically involves a process that includes anesthetizing a patient and the resecting of at least a portion of the cornea to expose the corneal stroma. A portion of the corneal stroma is then ablated using the laser system which performs an ablation dictated by the clinical ablation profile determined by the interface system.

What is claimed is:

1. An eye ablation data interface system, comprising:
   receiving means for receiving eye topography data;
   forming means for forming an eye ablation volume data set based on information received from said receiving means, and said means for forming including an aspherical ablation profile option means and a spherical ablation profile option means.

2. The system of claim 1 further comprising means for storing the eye ablation volume data set.

3. The system of claim 1 further comprising means for outputting said ablation volume data set to a means for ablating an eye based on said ablation volume data set.

4. The system of claim 3 wherein said means for ablating an eye includes a laser system.

5. The system of claim 4 wherein said laser system is a flying laser spot laser system.

6. The system of claim 4 wherein said laser system is a stationary large beam laser system.

7. The system of claim 1 further including viewing means for viewing a simulated implementation of one or both of said aspherical ablation profile option means and a spherical ablation profile option means.

8. The system of claim 7 wherein said viewing means includes means for simulateneously viewing the simulated, implementation of both of said aspherical ablation profile option means and said spherical ablation profile option means for comparison purposes.

9. The system of claim 8 wherein said viewing means illustrates the simulated implementation relative to an illustration of said eye topography data.

10. The system of claim 9 wherein said viewing means illustrates the simulated implementation of said aspherical and spherical ablation profile option means in color coded topographical level format and in two dimensional format.

11. The system of claim 9 further comprising means for choosing alternate cross-sectional views relative to a 360° view of said eye topography data in the simulated view of the simulated implementation of one or both of said aspherical and spherical ablation profile option means.

12. The system of claim 1 wherein said aspherical ablation profile option means and spherical ablation profile option means include a hyperopia correction pattern.

13. The system of claim 12 wherein the hyperopia correction pattern of said aspherical ablation profile option means includes interactive means for operator input for manipulating parameters of the hyperopia corrective pattern of said aspherical ablation profile option means.

14. The system of claim 13 wherein said interactive means includes fields for varying one or more of zone size, radius of curvature, interior diameter and exterior diameter of said pattern.

15. The system of claim 14 wherein said means for operator input includes each of said fields for varying.

16. The system of claim 12 wherein said means for inputting the aspherical presbyopic ablation profile includes interactive means for operator input for manipulating parameters of the presbyopic ablation profile.

17. The system of claim 16 wherein said interactive means for operator input includes fields for varying one or more of zone size, radius of curvature, interior diameter and exterior diameter.

18. The system of claim 17 wherein said means for operator input includes each of said fields for varying.

19. The system of claim 1 further comprising means for inputting an aspherical presbyopic ablation profile to said forming means.

20. The system of claim 1 further comprising interactive spherical ablation profile manipulation means for varying a configuration of a spherical ablation profile to be formed by said spherical ablation profile option means, and interactive aspherical ablation profile manipulation means for varying a configuration of an aspherical ablation profile to be formed by said aspherical ablation profile option means.

21. The system of claim 20 further comprising astigmatic profile option means and interactive astigmatic ablation profile manipulation means for varying a configuration of a astigmatic profile to be formed by said astigmatic ablation profile option means.

22. The system of claim 1 further comprising astigmatic profile option means for forming an astigmatic ablation profile upon an operator choosing activation of said astigmatic profile option means.

23. A method of forming an eye ablation volume data set for use with an eye laser system comprising feeding topographical data to the interface system of claim 1.

* * * * *